(12) United States Patent
Lim

(10) Patent No.: US 12,064,114 B2
(45) Date of Patent: Aug. 20, 2024

(54) GASTROINTESTINAL TISSUE APPROXIMATION CLIP (GI TAC) SYSTEM

(71) Applicant: Brian Lim, Irvine, CA (US)

(72) Inventor: Brian Lim, Irvine, CA (US)

( * ) Notice: Subject to any disclaimer, the term of this patent is extended or adjusted under 35 U.S.C. 154(b) by 723 days.

(21) Appl. No.: 17/148,455

(22) Filed: Jan. 13, 2021

(65) Prior Publication Data

US 2021/0212687 A1 Jul. 15, 2021

Related U.S. Application Data

(60) Provisional application No. 62/960,619, filed on Jan. 13, 2020.

(51) Int. Cl.
*A61B 17/08* (2006.01)
*A61B 17/00* (2006.01)
*A61B 17/04* (2006.01)
*A61B 17/10* (2006.01)
*A61B 17/295* (2006.01)

(52) U.S. Cl.
CPC ........ *A61B 17/083* (2013.01); *A61B 17/0467* (2013.01); *A61B 17/0469* (2013.01); *A61B 17/10* (2013.01); *A61B 17/295* (2013.01); *A61B 2017/0034* (2013.01); *A61B 2017/00473* (2013.01); *A61B 2017/00818* (2013.01); *A61B 2017/00876* (2013.01); *A61B 2017/0488* (2013.01); *A61B 2017/081* (2013.01)

(58) Field of Classification Search
None
See application file for complete search history.

(56) References Cited

U.S. PATENT DOCUMENTS

| | | | |
|---|---|---|---|
| 8,540,735 B2* | 9/2013 | Mitelberg | A61B 17/0485 606/232 |
| 9,107,654 B2* | 8/2015 | Chang | A61B 17/0401 |
| 11,446,023 B2* | 9/2022 | Binmoeller | A61B 17/07207 |
| 2001/0049497 A1* | 12/2001 | Kalloo | A61B 1/2736 600/114 |
| 2005/0075654 A1* | 4/2005 | Kelleher | A61B 17/0401 606/151 |
| 2005/0143760 A1* | 6/2005 | Imran | A61F 5/0003 606/142 |
| 2005/0192599 A1* | 9/2005 | Demarais | A61F 5/0086 606/151 |
| 2005/0192629 A1* | 9/2005 | Saadat | A61F 5/0076 606/221 |

(Continued)

*Primary Examiner* — Shaun L David
(74) *Attorney, Agent, or Firm* — Maier & Maier, PLLC

(57) ABSTRACT

A gastrointestinal tissue approximation clip system for approximating tissue defects, which includes an applicator that is sized to travel through an instrument channel of an endoscope; first and second tissue approximation clips that are transported to first and second locations of a tissue defect respectively by the applicator to approximate the tissue defect; first and second sutures attached to the first and second tissue approximation clips respectively; a clip approximation means for approximating the first and second tissue approximation clips. The clip approximation means and the first and second tissue approximation clips are sized to travel through the instrument channel, and the first and second tissue approximation clips are adapted to be detachably coupled to the applicator.

17 Claims, 22 Drawing Sheets

(56) References Cited

U.S. PATENT DOCUMENTS

| | | | |
|---|---|---|---|
| 2005/0251162 A1* | 11/2005 | Rothe | A61B 1/0014 606/153 |
| 2005/0277945 A1* | 12/2005 | Saadat | A61B 17/06166 606/108 |
| 2007/0049942 A1* | 3/2007 | Hindrichs | A61B 17/1285 623/13.14 |
| 2009/0125039 A1* | 5/2009 | Mikkaichi | A61B 17/0469 606/144 |
| 2010/0106166 A1* | 4/2010 | Cropper | A61B 17/0401 606/232 |
| 2012/0283757 A1* | 11/2012 | Miller | A61F 2/2445 606/151 |
| 2013/0178899 A1* | 7/2013 | Chang | A61B 17/0401 606/232 |
| 2013/0217957 A1* | 8/2013 | Maahs | A61B 17/12013 600/37 |
| 2020/0178956 A1* | 6/2020 | Mitelberg | A61B 17/0469 |
| 2021/0128140 A1* | 5/2021 | Wales | A61B 17/0467 |
| 2021/0128141 A1* | 5/2021 | Deuel | A61B 17/0467 |
| 2021/0267584 A1* | 9/2021 | Mitelberg | A61B 17/0401 |
| 2021/0275166 A1* | 9/2021 | Mitelberg | A61B 17/0469 |

* cited by examiner

FIG. 7B
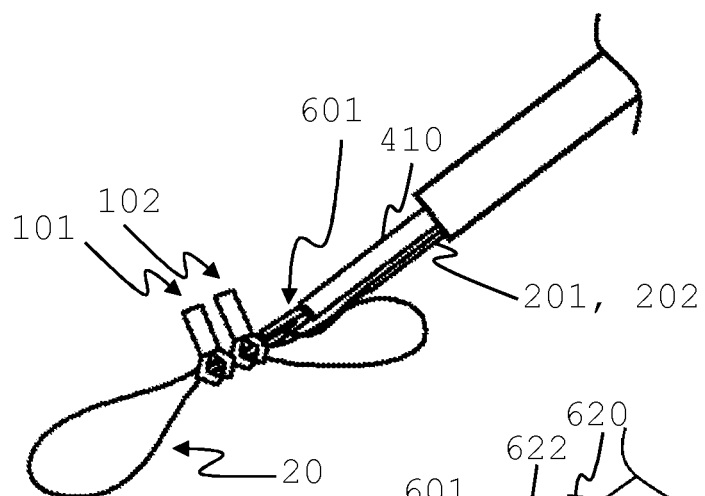
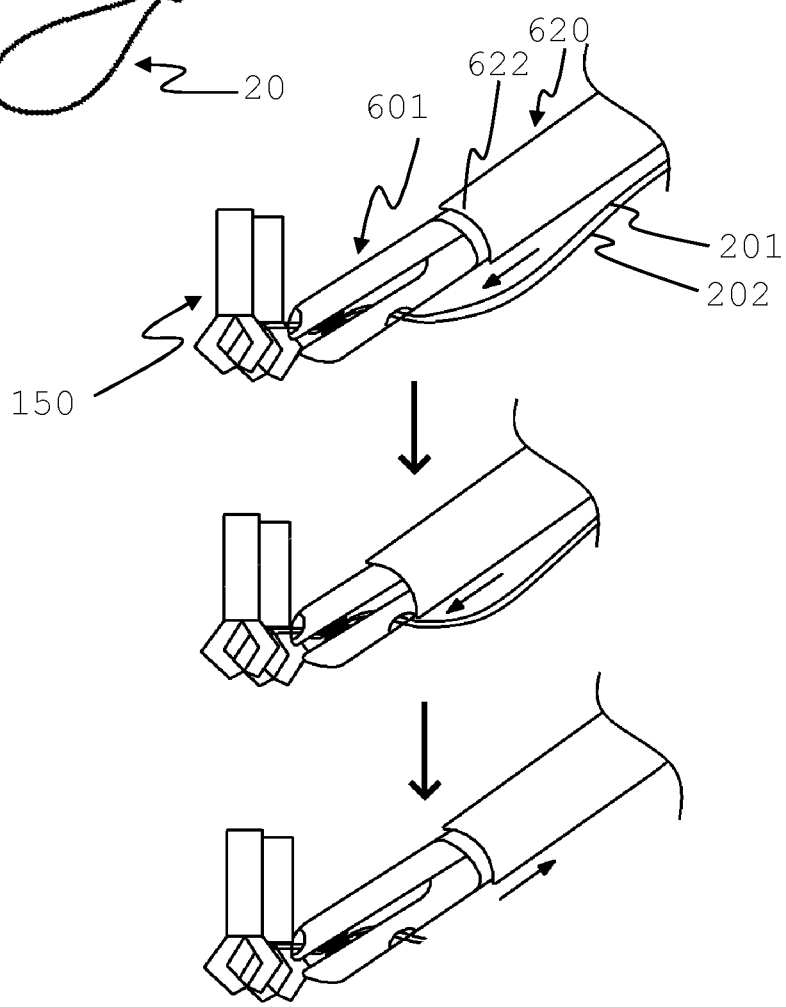
FIG. 7C
FIG. 7D
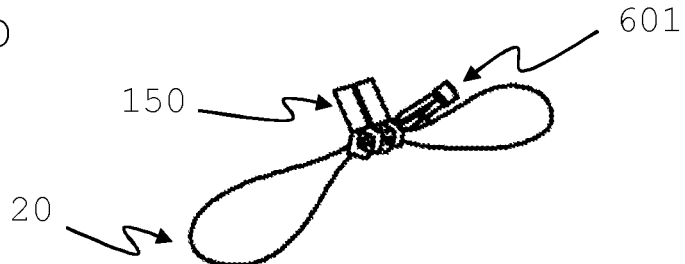

GASTROINTESTINAL TISSUE APPROXIMATION CLIP (GI TAC) SYSTEM

CROSS-REFERENCE TO RELATED APPLICATIONS

This application claims priority to U.S. provisional patent application No. 62/960,619 that was filed on Jan. 13, 2020, the disclosure of which is incorporated herein by reference in its entirety.

FIELD OF THE INVENTION

The present invention relates to gastrointestinal tissue approximation clip system, and more particularly, a gastrointestinal tissue approximation clip system and a method for closing large defects as found in certain indications in gastroenterology.

The field of gastroenterology is expanding rapidly due to the practice broadening its scope. One of the areas in gastroenterology that has been rapidly developing is endoscopic resection of different gastrointestinal (GI) abnormalities including (but not limited to) polyps, early cancer, and other lesions (abnormal growths) associated with GI indications.

A few different resection techniques have been developed so far, which include (but are not limited to) endoscopy mucosal resection (EMR), endoscopic submucosal dissection (ESD), endoscopic full-thickness resection (EFTR), and submucosal tunneling endoscopic resection (STER). However, the above techniques may be fraught with a few complications. Two of the most common are bleeding and perforation of the tissue. For either complication, a well-trained gastroenterologist would initially attempt a closure of the defect with endoscopic clip(s) (essentially bringing tissue edges in close apposition that is akin to suturing), or clipping of the blood vessel(s). There are also combined GI-surgery procedures such as Natural Orifice Transluminal Endoscopic Surgery (NOTES) where an opening on the gastrointestinal wall is intentionally created to go beyond the GI tract and perform surgery on structures such as the gallbladder. The opening itself has to be closed off at the end of this procedure.

However, there are several drawbacks to the endoscopic clips and devices known in the art, some of which will be discussed although they do not represent an exhaustive list of all of the clips and devices known in the art. Traditional endoscopic clips 10, as shown in FIG. 1, are rather limited in their application with regards to closing large perforations/defects because approximating the edges of such large defects can be extremely difficult, if not impossible, due to the limitation of the small diameters of their jaws (as shown in the jaw 15 of FIG. 1). Other clips were devised to close such large defects; one such clip is a larger variation that is attached on tip of the endoscope, i.e. over-the-scope clip. However, due to the large size of these clips, the gastroenterologist would have to take the endoscope out of the patient and spend time to place the larger clip on the tip of the endoscope and then re-introduce the endoscope with the larger clip attached thereon back into the patient. Such large clips traditionally required a therapeutic endoscope that is thicker in diameter to other endoscopes to accommodate the larger clip size. Furthermore, a device placed over the endoscope can increase the bulk of the endoscope when re-introducing the endoscope and the clip into the patient thus making the procedure more difficult, time consuming, and potentially risky. In addition, use of a shorter endoscope, referred to as either an "upper endoscope" or "gastroscope," is required for these large clips; this is limiting due to the upper endoscope's shorter length than traditional endoscopes, which in turn means that the upper endoscope can be introduced into the patient only to a certain distance resulting in some locations, e.g. proximal colon, likely being outside of its range.

Another device has been developed to emulate surgical suturing to close a defect tightly. However, the gastroenterologist would still be required to take the endoscope out of the patient to place this suturing device on the tip of the endoscope and re-introduce into the patient the endoscope with the suturing device attached thereon. Additionally, this suturing device requires a therapeutic endoscope with all of its attendant drawbacks as described above along with the upper endoscope. Thus, this suturing device requires placement over the endoscope, which in turn increases the bulk of the endoscope when re-introducing the endoscope and the suturing device into the patient for closure of the defect. The therapeutic endoscope for the suturing device only comes in a shorter scope length, which further limits the distance that this device can reach, meaning locations such as the proximal colon and much of the small intestine are likely to be inaccessible with the suturing device. Additionally, this device operates quite differently from traditional clips or large clips. Thus, the usage of this device requires training sessions, repeat training session(s) if not used often and the gastroenterologist needs to be reminded of how the suturing device operates, and more effort overall than other devices.

Alternatives to the above listed devices include emergent surgery, interventional radiology (IR) procedure for uncontrollable bleeding, observation with antibiotics and nil per os (NPO) status to see if the defect would close on its own. However, these procedures are either highly invasive or require longer observation periods, and thus, longer and costlier hospital stays. If these devices fail, much time will be required before alternatives such as surgery can be performed; thus, there will be increased risk for the patient, including death, through evolution into a clinical scenario such as pneumoperitoneum, pneumothorax, tension pneumothorax, etc.

Accordingly, in view of the problems described above, there exists a need for a tissue approximation system that allows the physician to close large GI defects quickly and efficiently, provides cost-savings, decrease complications for the patient, and would require little to no additional training. This invention is directed to solve these problems and satisfy a long-felt need.

SUMMARY OF THE INVENTION

The present invention contrives to solve the disadvantages of the prior art. The present invention is directed to a tissue approximation clip system.

An object of the present invention is to provide a gastrointestinal tissue approximation clip ("GI TAC") system for approximating tissue defects, the GI TAC system comprising: an applicator that is sized to travel through an instrument channel of an endoscope; first and second tissue approximation clips that are transported to first and second locations of a tissue defect respectively by the applicator to approximate the tissue defect; first and second sutures attached to the first and second tissue approximation clips respectively; and a clip approximation means for approximating the first and second tissue approximation clips. The clip approximation means is sized to travel through the instrument channel, the first and second tissue approximation clips are sized to travel through the instrument channel, and the first and second tissue approximation clips are adapted to be detachably coupled to the applicator.

Another object of the present invention is to provide a GI TAC system for approximating tissue defects, the GI TAC system comprising: an applicator that is sized to travel through an instrument channel of an endoscope; first and second tissue approximation clips that are transported to the first and second locations of a tissue defect respectively by the applicator to approximate the tissue defect; and first and second sutures attached to the first and second tissue approximation clips respectively. The first and second tissue approximation clips are sized to travel through the instrument channel, and the first and second tissue approximation clips are adapted to be detachably coupled to the applicator.

Still another object of the present invention is to provide a method for approximating a tissue defect using a GI TAC system, the method comprising the steps of: positioning a distal end of an insertion tube of an endoscope towards a tissue defect inside of a patient; directing, via an applicator, a first tissue approximation clip, detachably attached to the applicator, through an instrument channel of the endoscope and towards the tissue defect; placing the first tissue approximation clip on a first location of the tissue defect and clamping the first tissue approximation clip thereon; detaching the applicator from the first tissue approximation clip and withdrawing the applicator from the instrument channel of the endoscope; directing, via the applicator, a second tissue approximation clip, detachably attached to the applicator, through the instrument channel of the endoscope and towards the tissue defect; placing the second tissue approximation clip on a second location of the tissue defect and clamping the second tissue approximation clip thereon; and detaching the applicator from the second tissue approximation clip and withdrawing the applicator from the instrument channel of the endoscope. First and second sutures are attached to the first and second tissue approximation clips respectively. Furthermore, each of the first and second tissue approximation clips includes: a body portion; and a grasping portion coupled to the body portion. The body portion is detachably coupled to the applicator. The grasping portion includes a moveable jaw that is constructed to move from a spaced-apart position to an approximated position, or move from the approximated position to the spaced-apart position. The grasping portion is configured to grasp onto tissue during the placing steps.

The advantages of the present invention are: (1) the practitioner/physician does not need to take the endoscope out of the patient to use the GI TAC system; (2) practitioners/physicians and their assistants are familiar with using clips, thus the GI TAC system will be easy to use and quick to learn; (3) the clips are sized to fit through an instrument channel of an endoscope, thus removing the need for removal of the endoscope from the patient, fitting a device or clip over the distal end of the endoscope, and then re-introducing the endoscope, and its distal end, back into the patient; (4) time savings from not having to withdraw the endoscope out of the patient to use this invention, thus decreasing the risk of patient morbidity and mortality; (5) the GI TAC system and method can be deployed using scopes already in the market and operating rooms thus saving costs; (6) the GI TAC system and method can ensure precision equivalent to surgical staples that are still employed by practitioners/physicians; and (7) the simplicity of the GI TAC system and method in their application and the strength that the GI TAC system and method provide in approximating and holding tissues together.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein:

FIGS. 7A-E shows an alternative device for final deployment of the tissue approximation complex according to embodiments of the present invention;

DETAILED DESCRIPTION EMBODIMENTS OF THE INVENTION

Reference will now be made in detail to the preferred embodiments of the present invention, examples of which are illustrated in the accompanying drawings, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

Also, as used in the specification including the appended claims, the singular forms "a", "an", and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about", it will be understood that the particular value forms another embodiment.

Also, as used in the specification including the appended claims, "first and second sutures" may denote two individual suture strands, or first and second ends of a single suture strand.

Figure 1:
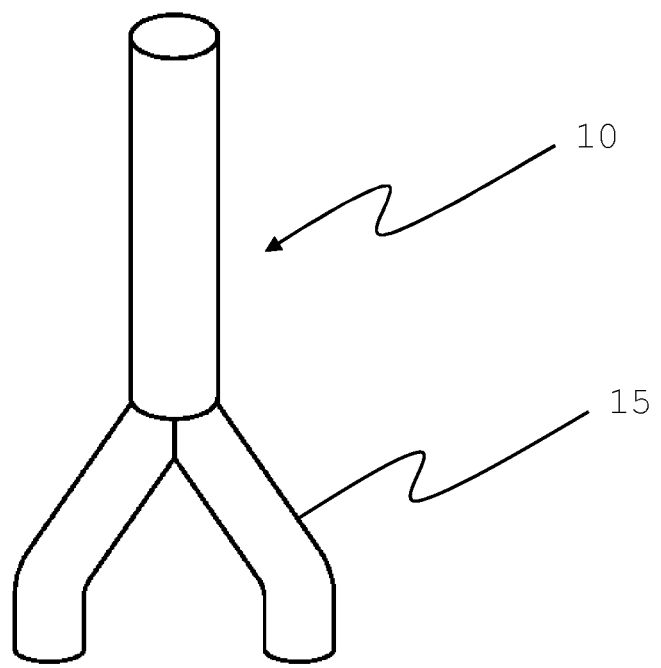
FIG. 1 shows a traditional endoscopic clip.
Figure 2A:
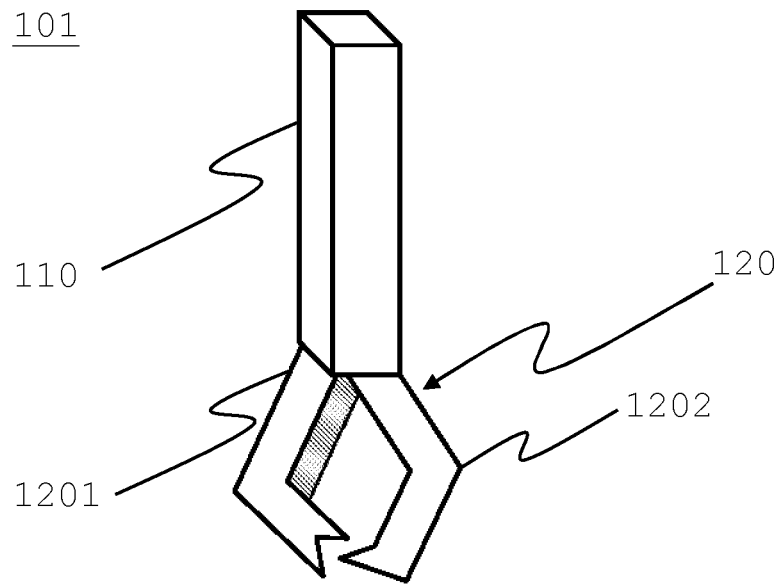
FIGS. 2A-B show tissue approximation clips according to embodiments of the present invention.

FIG. 2A shows a tissue approximation clip 101 for approximating tissue defects 20. The tissue approximation clip 101 includes a body portion 110 and a grasping portion 120 coupled to the body portion 110, wherein the grasping portion 120 includes a jaw having a first and second jaw portions 1201, 1202. The jaw of the grasping portion 120 is preferably of a rat-tooth type configuration as shown in FIG. 2A. The first and second jaw portions 1201, 1202 are constructed to move from a spaced-apart position to an approximated position, or move from the approximated position to the spaced-apart position. In the approximated position, the first and second jaw portions 1201, 1202 may be fully closed against each other or closed upon a portion of a tissue of a patient. Other designs and configurations with respect to the jaw portions 1201, 1202 of the grasping portion 120 may be considered that do not depart from the spirit and scope of the invention so long as the jaw is constructed to open and close whereupon closure of the jaw onto tissue provides sufficient clamping and hold onto the tissue.

The body portion 110 is detachably coupled to an applicator 400. Furthermore, the body portion 110 may be substantially cubic, substantially prismatic, substantially rectangular prism, substantially circular spherical, substantially oblate spheroidal, substantially prolate spheroidal, substantially columnar, or substantially cylindrical. Preferably, the body portion 110 is substantially cubic, substantially rectangular prism, or substantially prismatic. For the body portion 110 that is substantially spherical, substantially oblate spheroidal, substantially prolate spheroidal, substantially columnar, or substantially cylindrical, at least one surface of the body portion 110 is preferably substantially flat for ease of pairing one tissue approximation clip 101 with another tissue approximation clip 102. Overall, the tissue approximation clip 101 may be shorter and smaller than traditional clips 10 to permit the applicator 400 to bring the pair of tissue approximation clips 101, 102 to be closer to each other, minimizing the gap between the two approximation clips 101, 102, and thus, create a tighter closure of the tissue defect 20 itself.

Figure 2B:
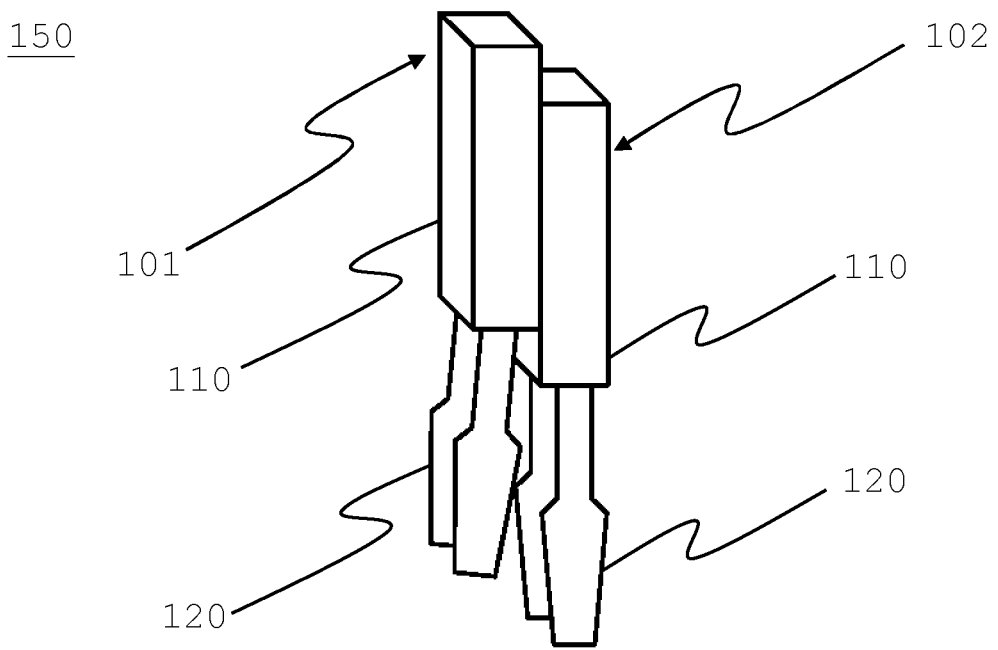

As shown in FIG. 2B, to further aid in the pairing of two tissue approximation clips 101, 102, the body portion 110 of a first tissue approximation clip 101 may be magnetic and the body portion 110 of a second tissue approximation clip 102 may be ferromagnetic, or vice versa. Alternatively, the grasping portion 120 of the first tissue approximation clip 101 may be magnetic and the grasping portion 120 of the second tissue approximation clip 102 may be ferromagnetic, or vice versa. Preferably, the body portions 110 of the first and second tissue approximation clips 101, 102 are magnetic and ferromagnetic respectively, or vice versa.

Figure 3A:
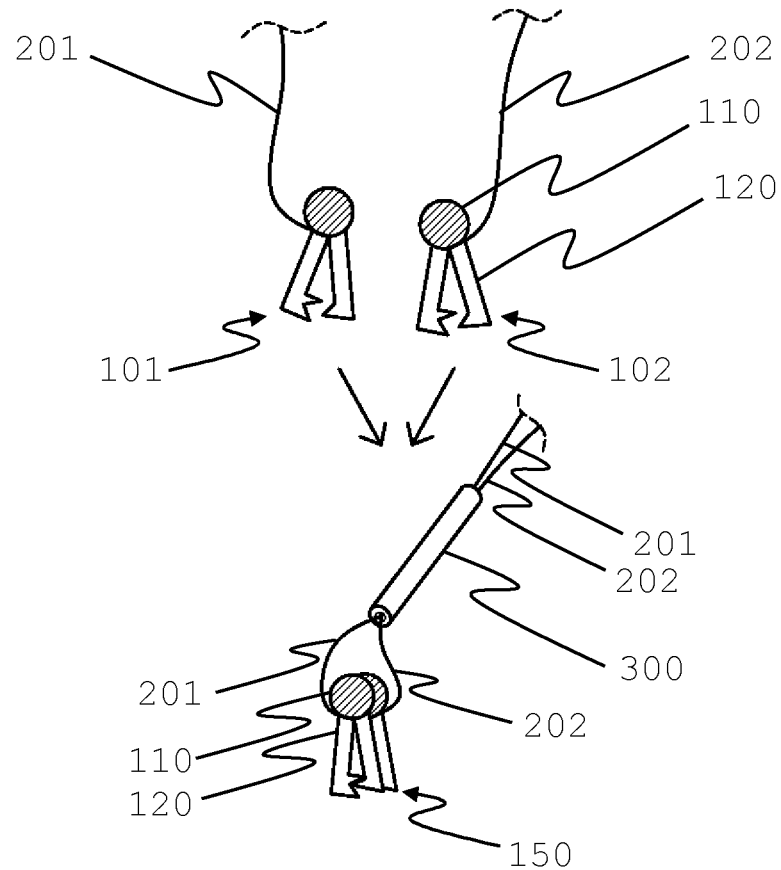
FIGS. 3A-D show approximation clips according to embodiments of the present invention with FIGS. 3A-B showing the formation of a tissue approximation clip complex.
Figure 3B:
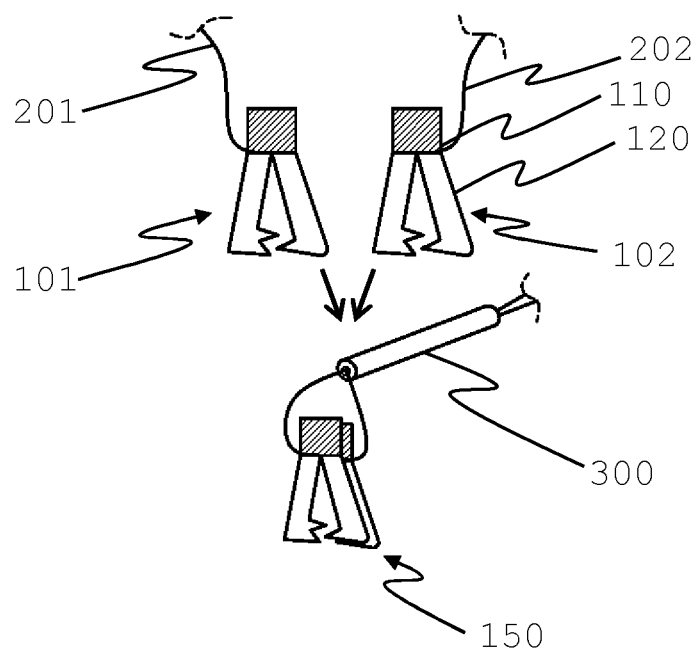
Figure 3C:
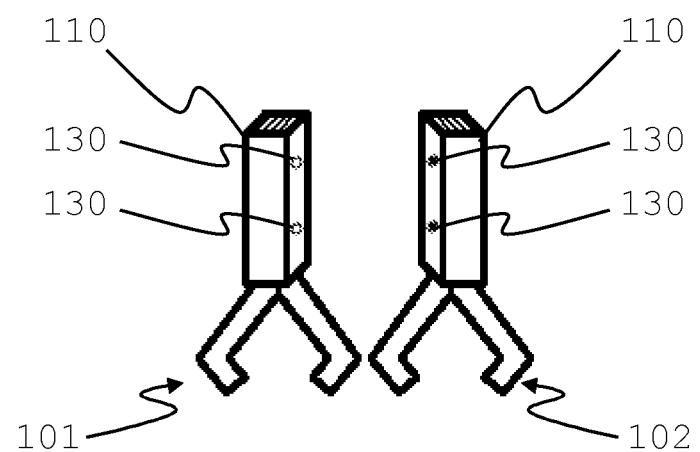
Figure 3D:
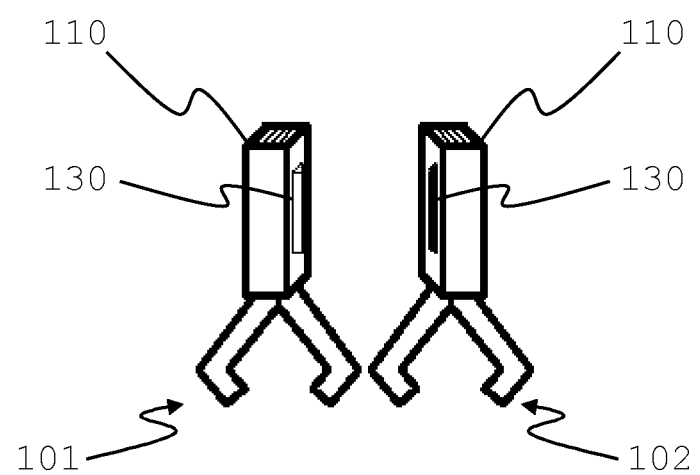

Additionally, the body portions 110 of the first and second tissue approximation clips 101, 102 may include joining means 130 as shown in FIGS. 3C-D. The joining means 130 are complimentary structures that allow the tissue approximation clips 101, 102 to collapse tightly onto each other upon magnetic attraction when they are brought close together. For example, as shown in FIG. 3C, the joining means 130 of the first tissue approximation clip 101 may be at least one substantially semi-spherical projection and the joining means 130 of the second tissue approximation clip 102 may be at least one groove constructed to receive the semi-spherical projection of the first tissue approximation clip 101, or vice versa. Alternatively, as shown in FIG. 3D, the joining means 130 of the first tissue approximation clip 101 may be one or more projecting ridges and the joining means 130 of the second tissue approximation clip 102 may be one or more grooves constructed to receive any of the projecting ridges of the first tissue approximation clip 101, or vice versa with the joining means 130 of the first tissue approximation clip 101 being one or more grooves and the joining means 130 of the second tissue approximation clip 102 being one or more projecting ridges. Alternatively, the joining means 130 of the first tissue approximation clip 101 may be at least one substantially prismatic projection and the joining means 130 of the second tissue approximation clip 102 (complimentary to the joining means 130 of the first tissue approximation clip 101) may be at least one groove constructed to receive therein the substantially prismatic projection of the first tissue approximation clip 101, or vice versa. Overall, the joining means 130 of one tissue approximation clip 101 may be a raised projection of any shape and number that is complimentarily received in the joining means 130 of the other tissue approximation clip 102. Furthermore, at least one face of the body portion 110 of a first tissue approximation clip 101 may feature a joining means 130 and at least one face of the body portion 110 of a second tissue approximation clip 102 may feature a joining means 130 that is complimentary to the joining means 130 of the first tissue approximation clip 101.

Overall, the tissue approximation clip 101 is shorter than traditional clips 10 in order to transport the tissue approximation clips 101, 102 to the hole/defect itself for a tighter closure. Additionally, the body portions 110 of the first and second tissue approximation clips 101, 102 of the tissue approximation clip system 100 may include the joining means 130 as described above. Other designs and configurations with respect to the jaw of the grasping portion 120 may be considered that do not depart from the spirit and scope of the invention so long as the jaw is constructed to open in a spaced-apart position (of varying degrees) and close in an approximated position whereupon closure of the jaw onto any position about the tissue defect 20 provides sufficient clamping to hold onto the clamped position of the tissue defect 20.

As shown in FIGS. 3A-B, a suture 201 is attached to the tissue approximation clip 101. The suture 201 can be made from any materials, or combination thereof, known in the art, which includes synthetic absorbables (e.g. polyglycolic acid, polylactic acid, Monocryl, and polydioxanone) and synthetic non-absorbables (nylon, polyester, PVDF and polypropylene). The suture 201 aids in the pairing of the tissue approximation clips 101 where tension (e.g. from a pull) is applied to the sutures 201, 202 (after the respective first and second tissue approximation clips 101, 102 are clamped to first and second positions of the tissue defect 20 respectively), which brings the clamped first and second tissue approximation clips 101, 102 closer together such that they eventually pair together (through magnetic attraction and/or other means) as shown in FIGS. 2B and 3A-B to form a tissue approximation complex 150. The suture 201 may be attached to the grasping portion 120 of the tissue approximation clip 101. Alternatively, the suture 201 is attached to the body portion 110 of the tissue approximation clip 101. Preferably, the suture 201 is attached to an area or a junction between the body portion 110 and the grasping portion 120 of the tissue approximation clip as shown in FIGS. 3A-B. Additionally, the body portion 110 also detachably couples to an applicator 400 as discussed below.

As shown in FIGS. 4A-L, a tissue approximation clip system 100 is provided. As shown, the tissue approximation clip system 100 includes an applicator 400 that is sized to travel through an instrument channel 310 of an endoscope 300; first and second tissue approximation clips 101, 102 that are transported to first and second locations of a tissue defect 20 respectively by the applicator 400 to approximate the tissue defect; first and second sutures 201, 202 attached to the first and second tissue approximation clips 101, 102 respectively; and a clip approximation means for approximating the first and second tissue approximation clips 101, 102. The clip approximation means is sized to travel through the instrument channel 310. The first and second tissue approximation clips 101, 102 are sized to travel through the instrument channel 310, and are adapted to be detachably coupled to the applicator 400.

Figure 4A:
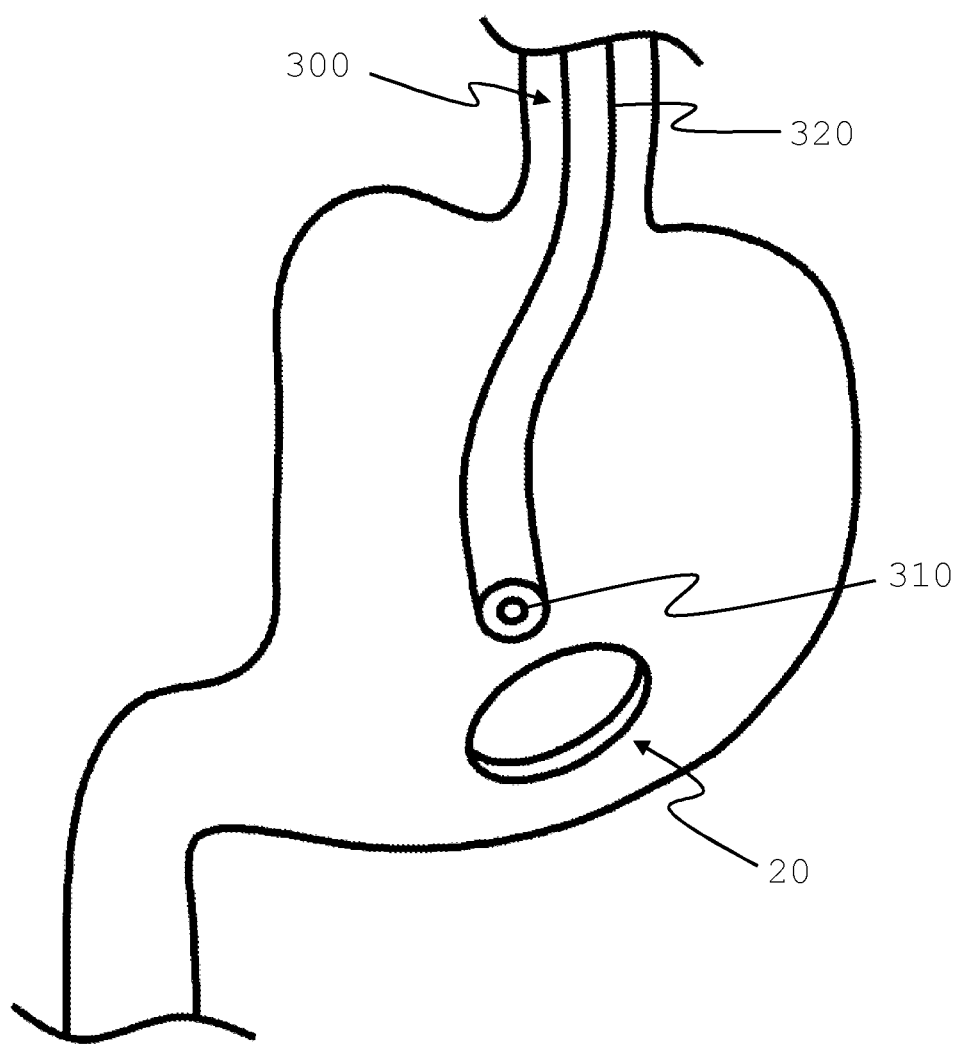
FIGS. 4A-L show a method for closure of a defect using a tissue approximation clip system according embodiments of the present invention.
Figure 4B:
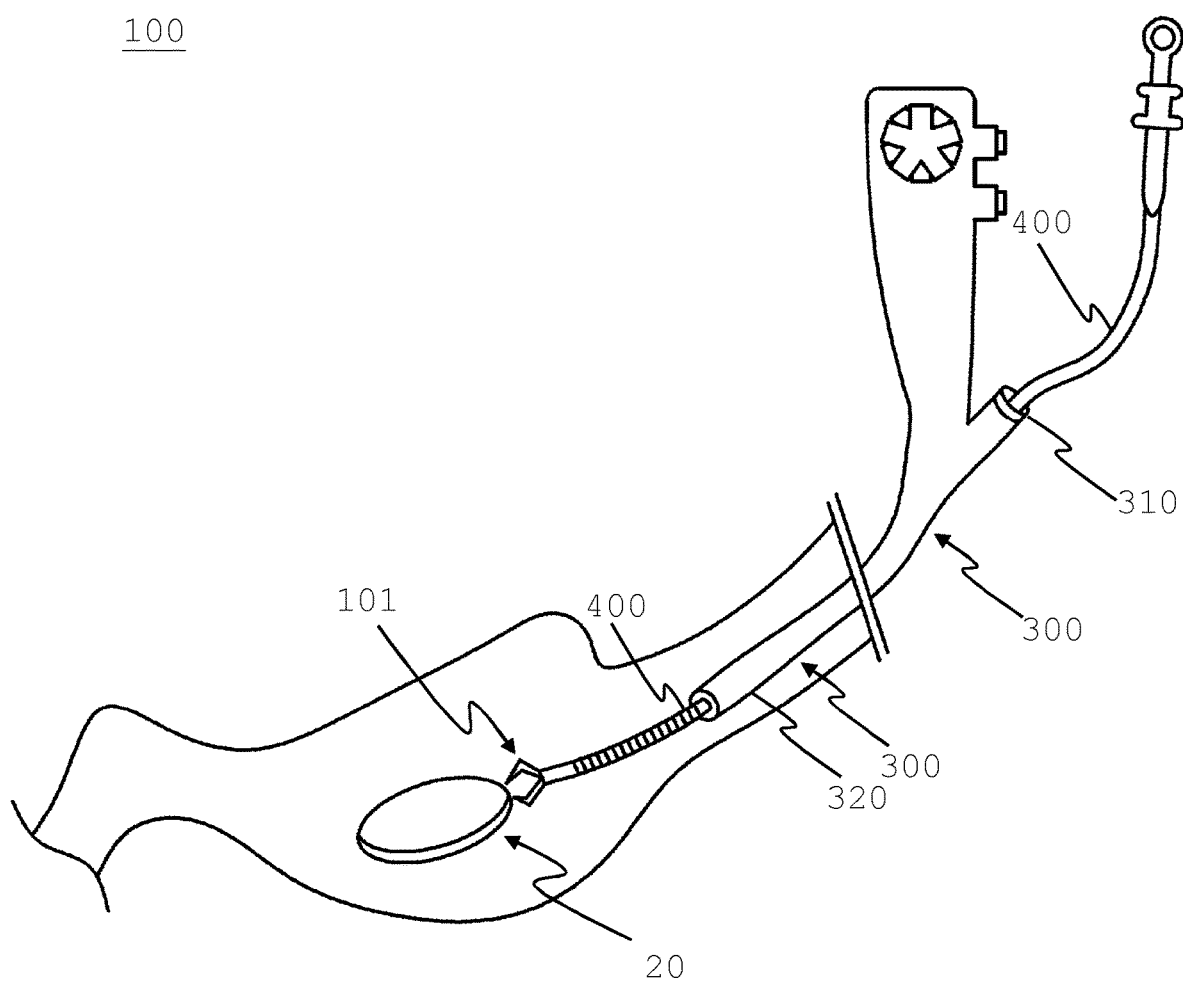
Figure 4C:
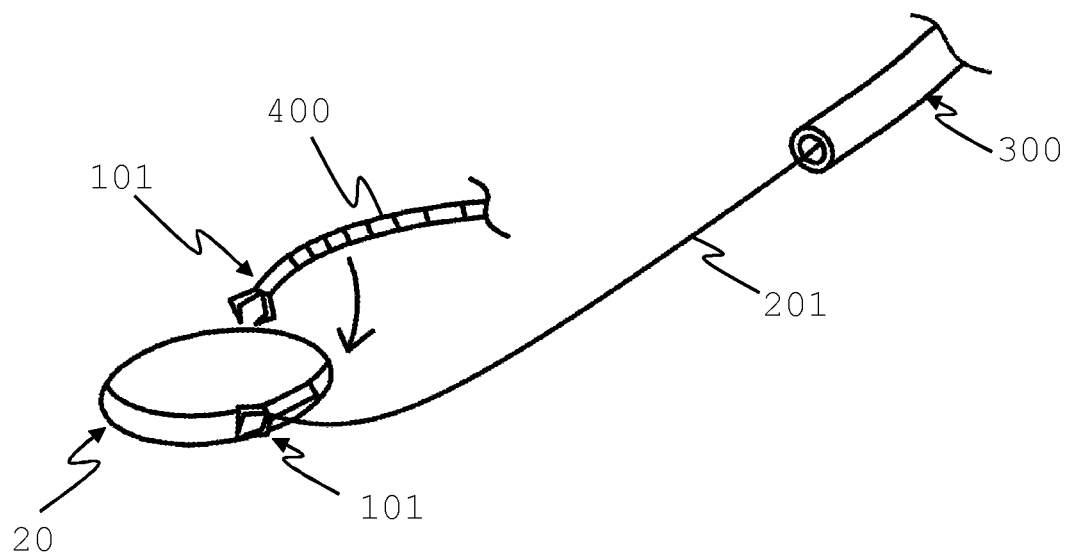
Figure 4D:
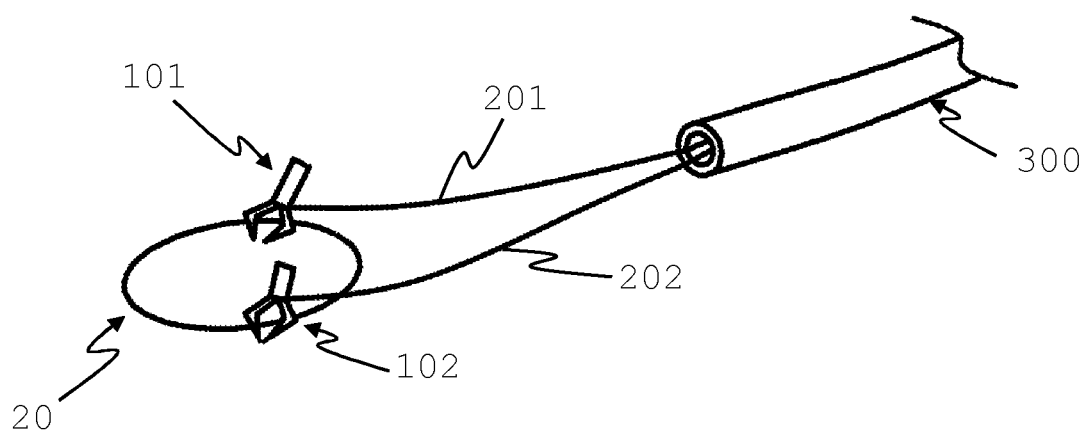

The endoscope 300 is introduced into the patient through an opening of the patient or an opening provided by an incision. As shown in FIG. 4A, the distal end of an insertion tube 320 of the endoscope 300 (i.e. the distal end of the endoscope 300) is directed towards the tissue defect 20. The tissue defect 20 shown in FIG. 4A and in other figures (here, a tear in the body wall of the stomach of a patient) is for illustrative purposes only. The tissue approximation system 100 can be used at any location that is accessible by the endoscope 300. As shown in FIGS. 4B-D, the applicator 400 transports the first and second tissue approximation clips 101, 102 (described above) individually and sequentially to first and second locations of the tissue defect 20 respectively. Also shown is how each of the first and second tissue approximation clips 101, 102 has a suture attached to thereon as described above. Specifically, the first suture 201 is attached to the first tissue approximation clip 101 as shown in FIGS. 4C and 4D prior to entry thereof into and transport through the instrument channel 310 of the endoscope 300, likewise for the second suture 202 and the second tissue approximation clip 102. The first suture 201 includes a proximal end and a distal end wherein the distal end of the first suture 201 attaches to the first tissue approximation clip 101 to be inserted into the instrumental channel 310 of the endoscope 300 and directed towards the first position of the tissue defect 20 via the applicator 400. Furthermore, the second suture 202 includes a proximal end and a distal end wherein the distal end of the second suture 202 attaches to the second tissue approximation clip 201 to be inserted into the instrumental channel 310 of the endoscope 300 and directed towards the second position of the tissue defect 20. Alternatively, the first and second sutures 201, 202 may denote opposite ends of a single suture.

Figure 4E:
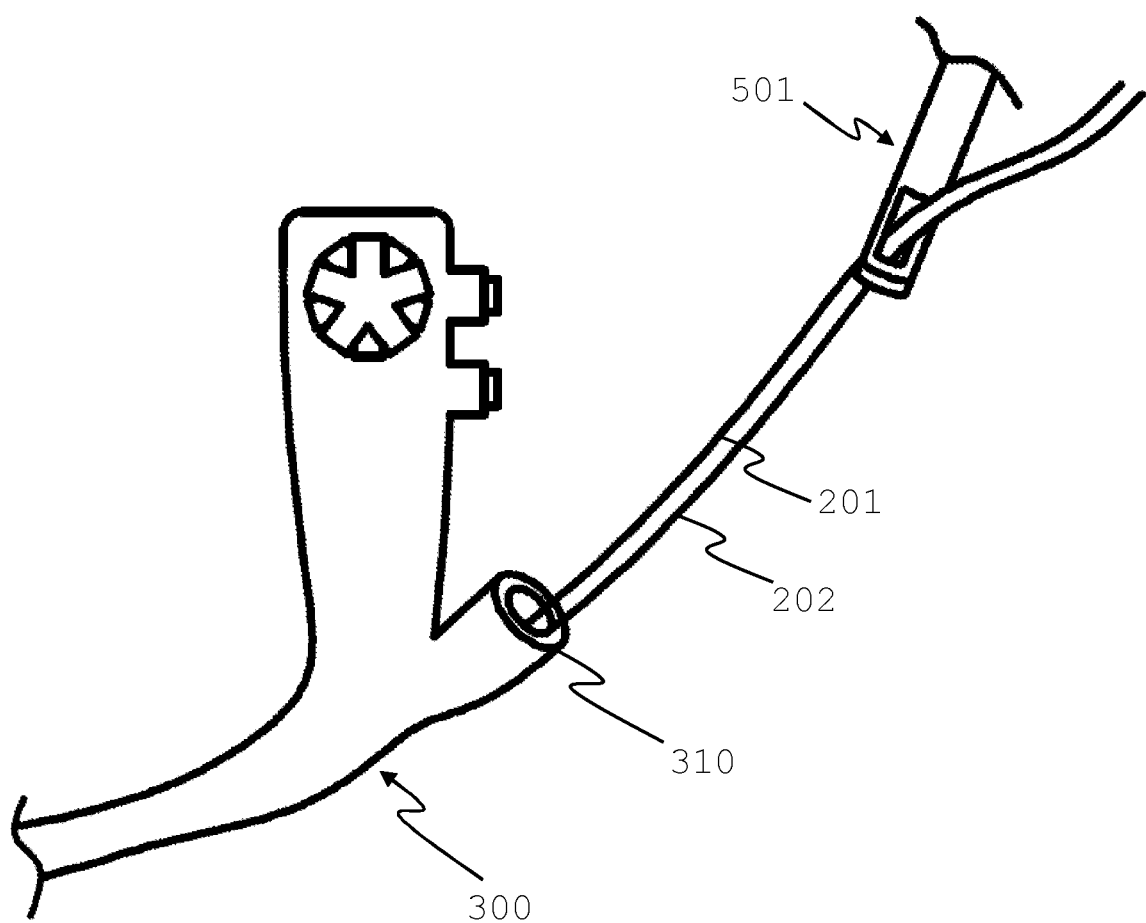
Figure 5:
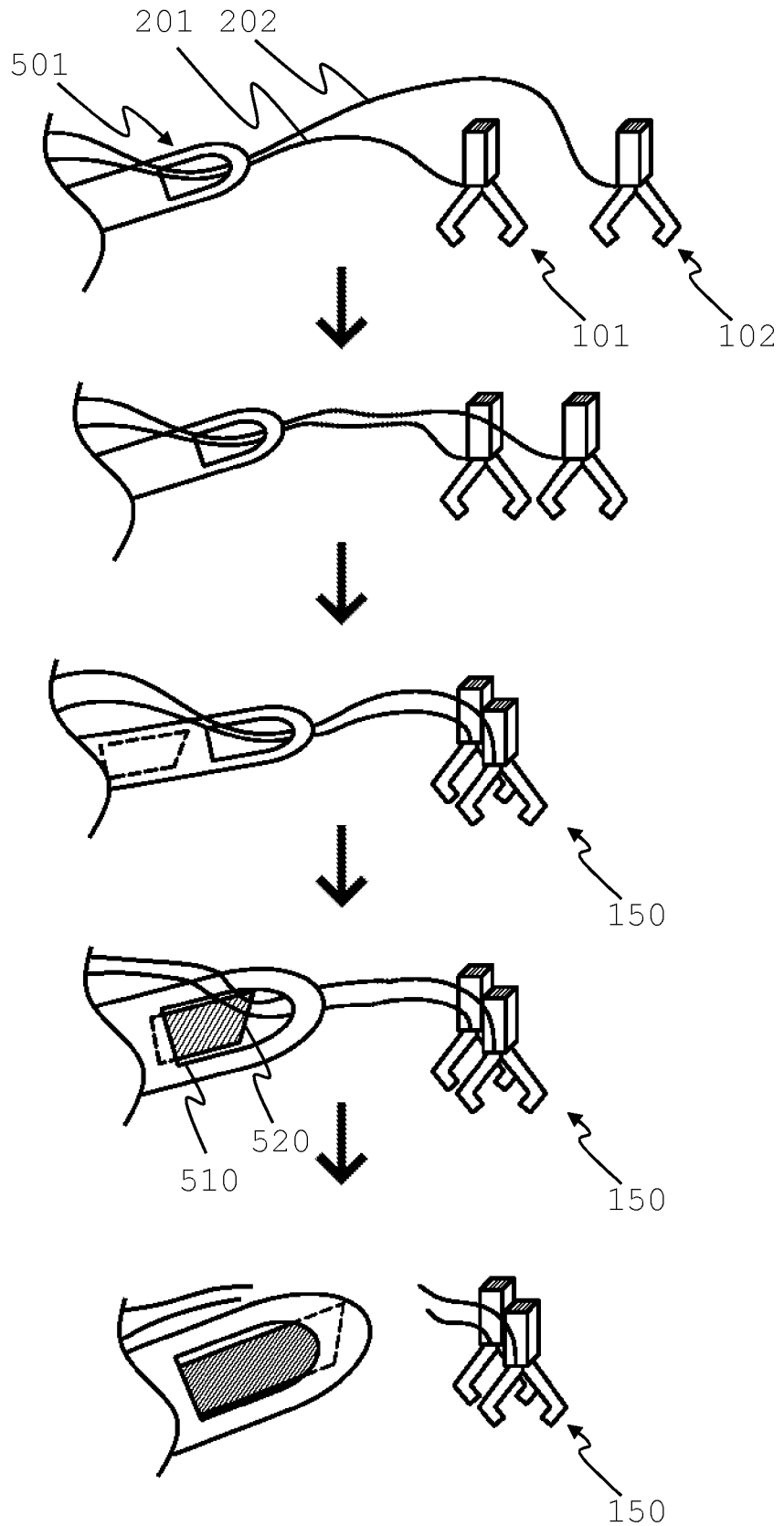
FIG. 5 shows a device for final deployment of the tissue approximation complex according to embodiments of the present invention.

The clip approximation means may be a catheter device 501 as shown in FIGS. 4E and 5, a catheter device 502 as shown in FIGS. 6A-E, or a suture adjoining clamp 601 as shown in FIGS. 7A-D. The catheter device 501 as shown in FIGS. 4E and 5 is disposed at distal end of its own applicator, the distal end of the applicator directed towards the tissue defect 20. As shown, the catheter device 501 includes a slidable blade 520 and a through-hole 510. The slidable blade 520 may be installed within the catheter device 501 and positioned about the through-hole 510 with the practitioner/physician controlling the slidable blade 520 of the catheter device 501. The through-hole 510 of the catheter device 501 permits the first and second sutures 201, 202 to pass therethrough, and the slidable blade 520 is to cut the first and second sutures 201, 202 from the first and second tissue approximation clips 101, 102 respectively.

When approaching the first and second tissue approximation clips 101, 102, the catheter device 501 tensions the first and second sutures 201, 202 such that they are brought closer together. By bringing the sutures 201, 202 closer together when the first and second sutures 201, 202 are tensioned and/or pulled, the first tissue approximation clip 101 approaches the second tissue approximation clip 201 and both of the tissue approximation clips 101, 201 substantially and magnetically couples to each other into a tissue approximation complex 150 as shown in the sequence depicted in FIG. 5.

Alternatively, as shown in FIGS. 6A-E, the clip approximation means may be a catheter device 502 which includes a slidable blade 520 and a through-hole 510. The slidable blade 520 may be installed within the catheter device 502 and positioned about the through-hole 510 with the practitioner/physician controlling the slidable blade 520 of the catheter device 502. The through-hole 510 of the catheter device 502 permits the first and second sutures 201, 202 to pass therethrough, and the slidable blade 520 is to cut the first and second sutures 201, 202 from the first and second tissue approximation clips 101, 102 respectively. Furthermore, as shown, the catheter device 502 further includes: a tube 505 which includes an end 512 and the through-hole 510; an inner rod 530 that extends from the tube 505; and a ball 540 detachably coupled to the inner rod 530. The end 512 of the tube 505 is open to permit the first and second sutures 201, 202 to pass through the opened end 512 of the tube 505.

Figure 6A:
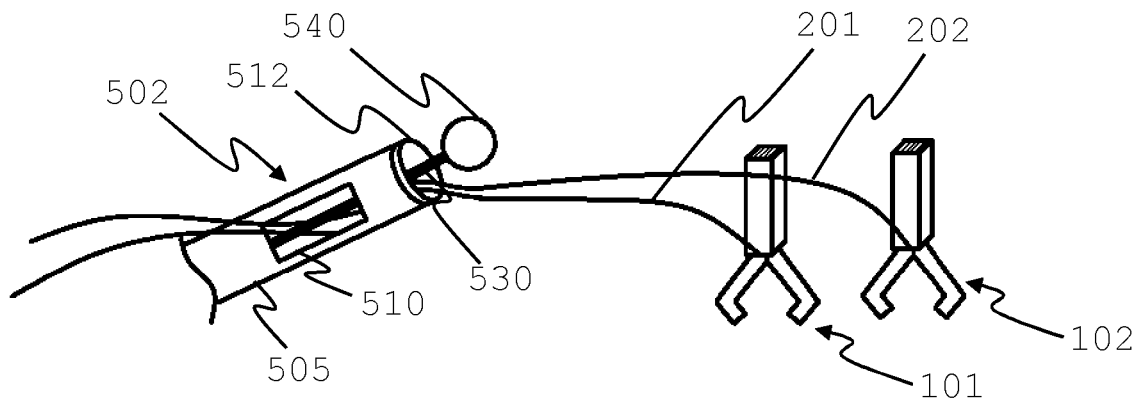
FIGS. 6A-E show an alternative device for final deployment of the tissue approximation complex according to embodiments of the present invention.
Figure 6B:
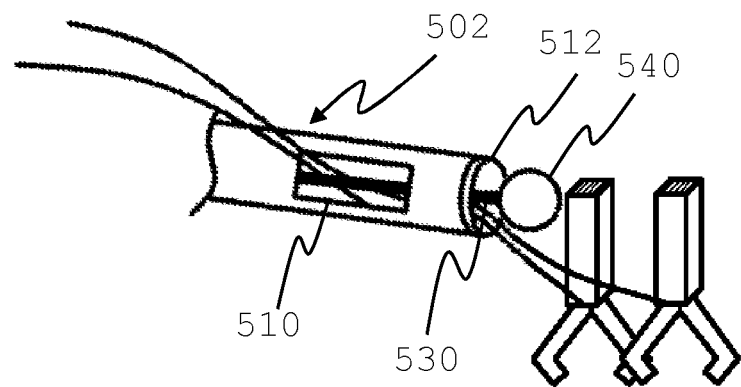
Figure 6C:
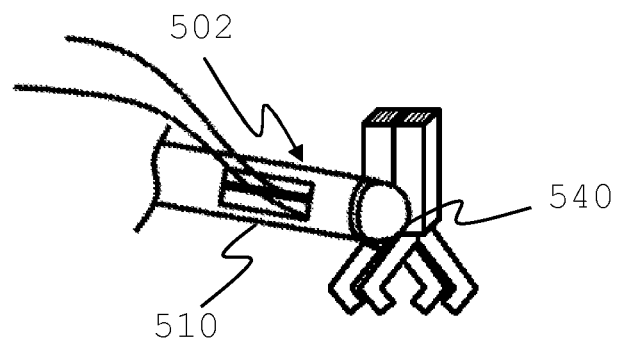
Figure 6D:
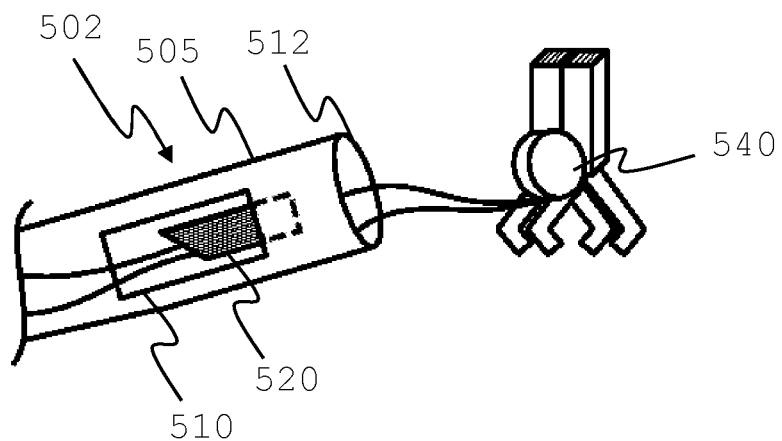
Figure 6E:
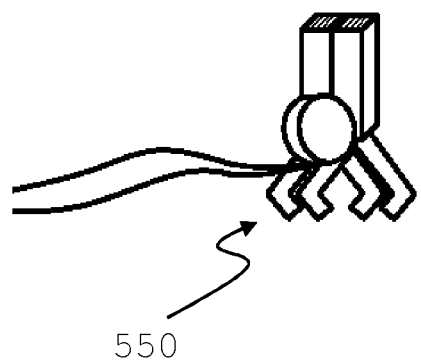

When the inner rod 530 is retracted to the tube 505 as shown in FIGS. 6B-C, the ball 540 is constructed to snap onto the first and second sutures 201, 202 to form a ball-and-socket complex 550 and detach from the inner rod 530. The inner rod 530 is in an extended position at first and then the practitioner/physician can retract the inner rod 530 back to the tube 505. The slidable blade 520 may be installed within the catheter device 502 and positioned about the through-hole 510 with the practitioner/physician controlling the slidable blade 520 of the catheter device 502. As shown FIG. 6D, the slidable blade 520, controlled by a handle positioned outside of the patient, is then used to cut the first and second sutures 201, 202 to release the ball-and-socket complex 550. As shown in FIG. 6E, the ball-and-socket complex 550 holds the first and second sutures 201, 202 tightly against the first and second tissue approximation clips 101, 102, thus pulling on the two tissue approximation clips 101, 102 tightly towards each other (i.e. the ball-and-socket complex 550 approximates the two approximation clips 101, 102). Therefore, the first and second tissue approximation clips 101, 102 need not be magnetically attracted to each other here, as the ball-and-socket complex 550 brings the first and second tissue approximation clips tightly to each other to form the tissue approximation clip complex 150.

Figure 7A:
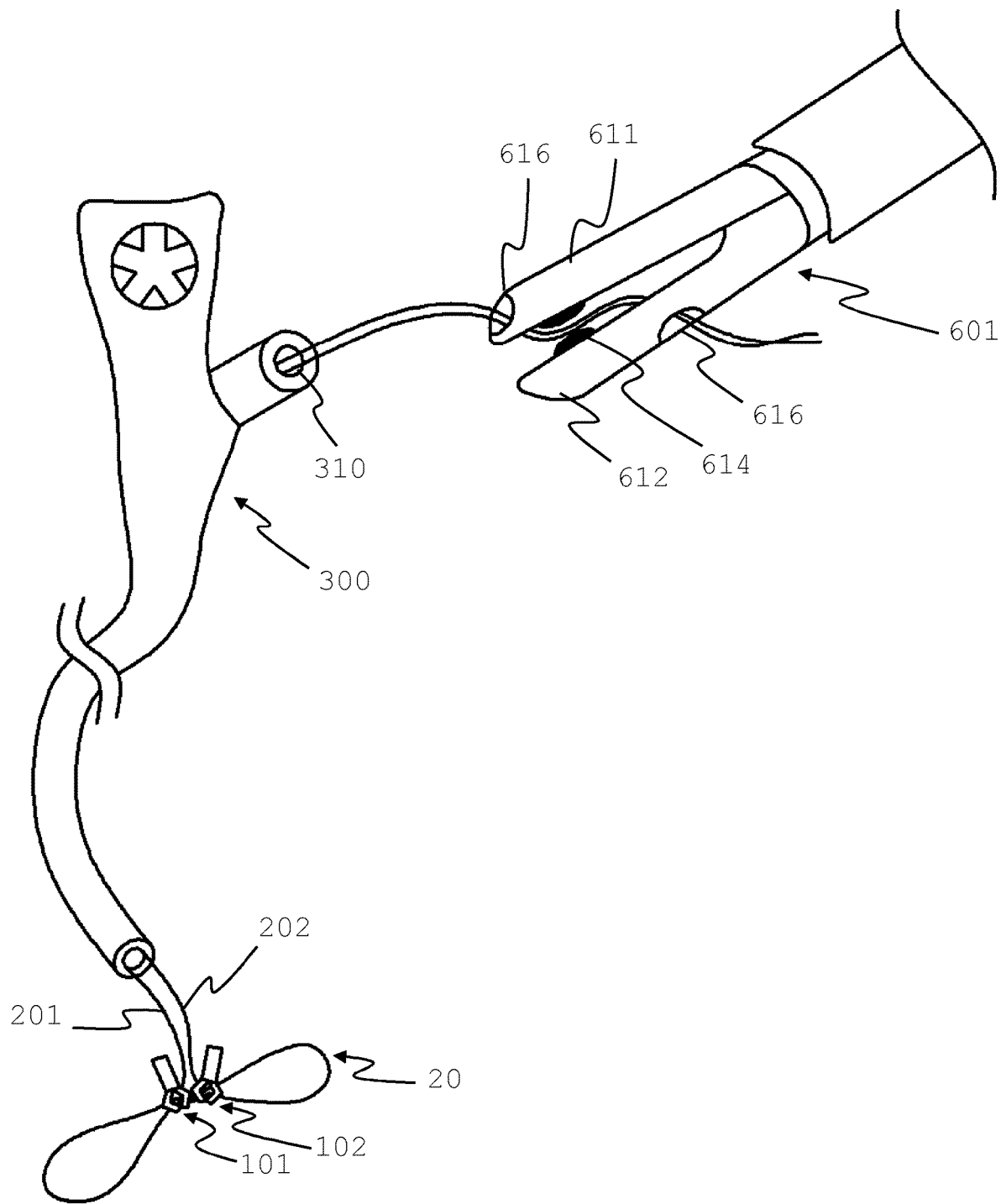
Figure 7E:
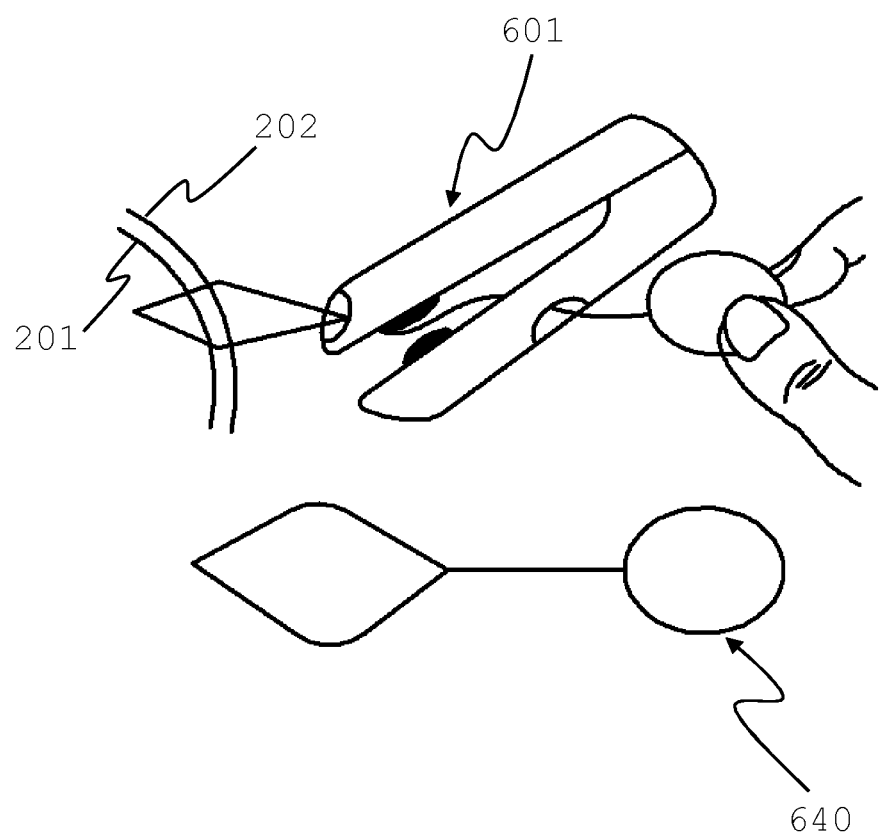

Alternatively, as shown in FIGS. 7A-D, the clip approximating means may be a suture adjoining clamp 601. The suture adjoining clamp 601 includes movable arms 611, 612 as shown in FIG. 7A. Each of the arms 611, 612 includes a grip 614 and a through-hole 616 through which threading of the first and second sutures 201, 202 are permitted. To thread the sutures 201, 202 through the suture adjoining clamp 601, a pre-loaded suture threader 640 may be used as shown in FIG. 7E. The arms 611, 612 of the suture adjoining clamp 601 are movable from a spaced-apart position to an approximated position, and movable from the approximated position to the spaced-apart position. Furthermore, the suture adjoining clamp 601 does not have to open wide. Additionally, the suture adjoining clamp 601 may configured with a half-way lock or soft lock for the arms 611, 612 so that the suture adjoining clamp 601 may be pushed down the instrument channel 310 using a suture adjoining clamp applicator 410 without getting caught somewhere while travelling through the instrument channel 310 towards the tissue defect 20. The suture adjoining clamp applicator 410 is similar to the applicator 400 described above. As shown in FIGS. 7B-C, once at the tissue approximation complex 150, the suture adjoining clamp 601 may be brought up against the tissue approximation complex 150 and then clamped down.

When, the first and second sutures 201, 202 are between the grips 614, and the arms 611, 612 are in the approximated position, the grips 614 meet each other and firmly hold down the first and second sutures 201, 202 as shown in FIG. 7C. The grips 614 may be made from any material known in the art. Preferably, the grips 614 are made of soft material such as rubber.

As shown in FIGS. 7A-D, when the suture adjoining clamp 601 is used to approximate the first and second tissue approximation clips 101, 102, a cutting means 620 for cutting the first and second sutures 201, 202 is deployed. As shown in FIGS. 7A-C, the suture adjoining clamp applicator 410 may further include the cutting means 620 in the form of a slidable sheath 620 having a sharpened outer edge 622. A width of the slidable sheath 620 is greater than a width of the suture adjoining clamp 601. Accordingly, the outer edge 622 of the slidable sheath 620 is configured to slide across the first and second sutures 201, 202 that are presented by at least one of the through-holes 616 of the arms 611, 612 to cut the first and second sutures 201, 202.

Figure 8:
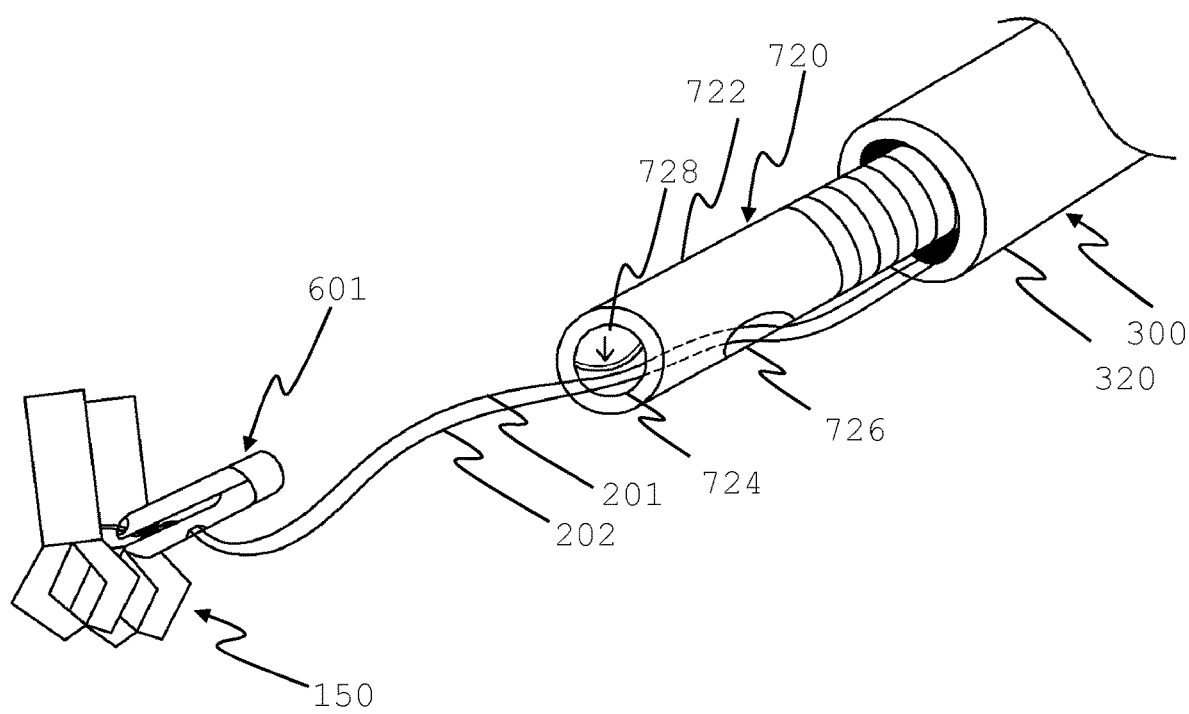
FIG. 8 shows a cutting device according to embodiments of the present invention.

Alternatively, as shown in FIG. 8, the cutting means 620 may be a cutting device 720 which includes a tube 722 having an end 724; a side through-hole 726; and a cutting blade 728 that is constructed to slide down to close the end 724 or slide up to open the end 724. The first and second sutures 201, 202 are threaded through the open end 724 and the side through-hole 726 when the blade 728 is pulled up; the threading process may be aided by the pre-loaded suture threader 640 as shown in FIG. 7E. As shown in FIG. 8, the cutting device 720 is sized to pass through the instrument channel 310 of the endoscope 300 with the end 724 of the cutting device 720 being directed towards the tissue defect 20. Procedurally, when the suture adjoining clamp 601 is used, the device 720 follows the suture adjoining clamp applicator 410 after the latter transported the suture adjoining clamp 601 to the first and second clips 101,102 to approximate the first and second clips 101, 102 into a tissue approximation complex 150 and adjoin the suture adjoining clamp 601 to the tissue approximation complex 150. The cutting blade 728 cuts the first and second sutures 201, 202 when the cutting blade 728, controlled by the practitioner/physician, slides down upon the first and second sutures 201, 202 to close the end 724. Since the first and second sutures 201, 202 can be brought together using the suture adjoining clamp 601, there is no need to target the sutures 201, 202 individually at the GI lumen level as one would have to with other cutting devices.

The cutting device 720 shown in FIG. 8 may be adapted to be used with the catheter device 501 similar to that shown in FIGS. 4E and 5 and the catheter device 502 similar to that shown in FIGS. 6A-E. The catheter device 501, as shown in FIGS. 4E and 5, and the catheter device 502, as shown in FIGS. 6A-E, are disposed at distal end of their own applicator 400, the distal end of the applicator 400 directed towards the tissue defect 20. As shown, the catheter devices 501 and 502 include a through-hole 510. The through-holes 510 of the catheter devices 501, 502 permit the first and second sutures 201, 202 to pass therethrough.

When approaching the first and second tissue approximation clips 101, 102, the catheter device similar to the catheter device 501 tensions the first and second sutures 201, 202 such that they are brought closer together. By bringing the sutures 201, 202 closer together when the first and second sutures 201, 202 are tensioned and/or pulled, the first tissue approximation clip 101 approaches the second tissue approximation clip 201 and both of the tissue approximation clips 101, 201 (constructed here to magnetically attract each other) substantially and magnetically couples to each other into a tissue approximation complex 150 similar to the sequence depicted in FIG. 5 but without the depicted slidable blade 520. The cutting device 720 as shown in FIG. 8 may be threaded with the first and second sutures 201, 202 and transported through the instrument channel 310 of the endoscope 300 towards the tissue approximation complex 150. Without the need for the practitioner/physician to grab the sutures 201, 202 and position them within the cutting devices known in the art at the level of the tissue defect 20, which may prove to be challenging to the practitioner/physician. Rather, the cutting means 720 is advantageous for grabbing the sutures 201, 202 at the level of the port 330 of the instrument channel 310 and allows capturing of both sutures 201, 202 at the same time; the port 330, as shown in FIG. 8A, is disposed at or about the proximal end of the instrument channel 310, whereas the distal end of the instrument channel 310 lies at or about the distal end of insertion tube 320.

The cutting device 720 shown in FIG. 8 may be adapted to be used with the catheter device 502 similar to that shown in FIGS. 6A-E. The catheter device 502 here further includes a tube 505 which includes an end 512 and a through-hole 510; an inner rod 530 that extends from the tube 505; and a ball 540 detachably coupled to the inner rod 530. The end 512 of the tube 505 is open to permit the first and second sutures 201, 202 to pass through the opened end 512 of the tube 505. The through-hole 510 of the catheter device 502 permits the first and second sutures 201, 202 to pass therethrough. After the ball 540 substantially adjoins the first and second tissue approximation clips 101, 102 as shown in FIG. 6C, the inner rod 530 is detached from the ball 540. The catheter device 502 is then pulled back away from the tissue defect. The cutting device 720, as shown in FIG. 8, may be threaded with the first and second sutures 201, 202 and transported through the instrument channel 310 of the endoscope 300 towards the ball 540 substantially adjoined to the first and second tissue approximation clips 101, 102. Without the need to approach the tissue approximation complex 150, the operator of the cutting device 720 may cut the first and second sutures at a distance from the tissue approximation complex 150 to release the ball 540 and the first and second tissue approximation clips 101, 102 as a ball-and-socket complex 550 as shown in FIG. 6E.

Figure 9A:
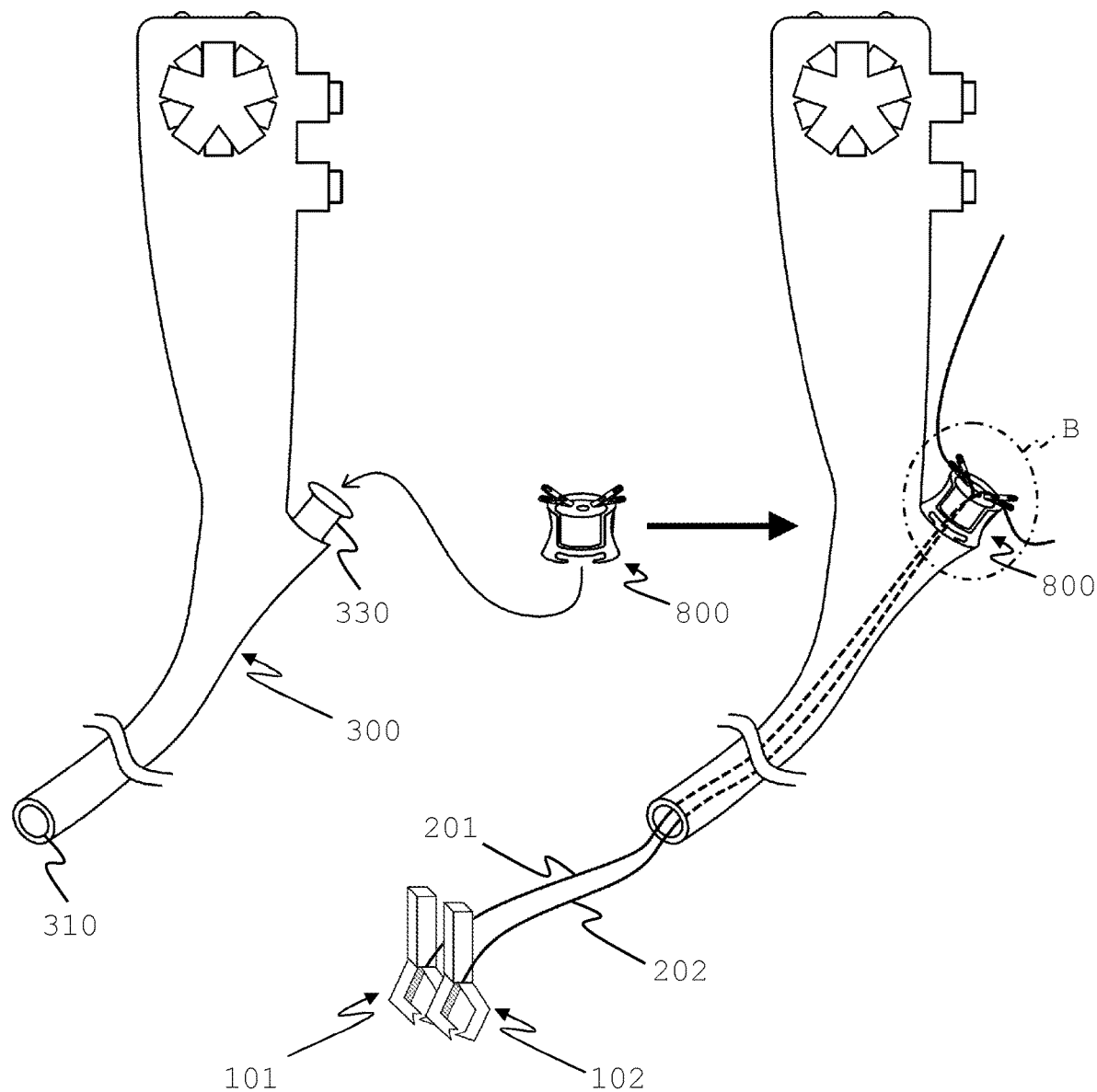
FIGS. 9A-C show a device for use with the tissue approximation clip system according to embodiments of the present invention.
Figure 9B:
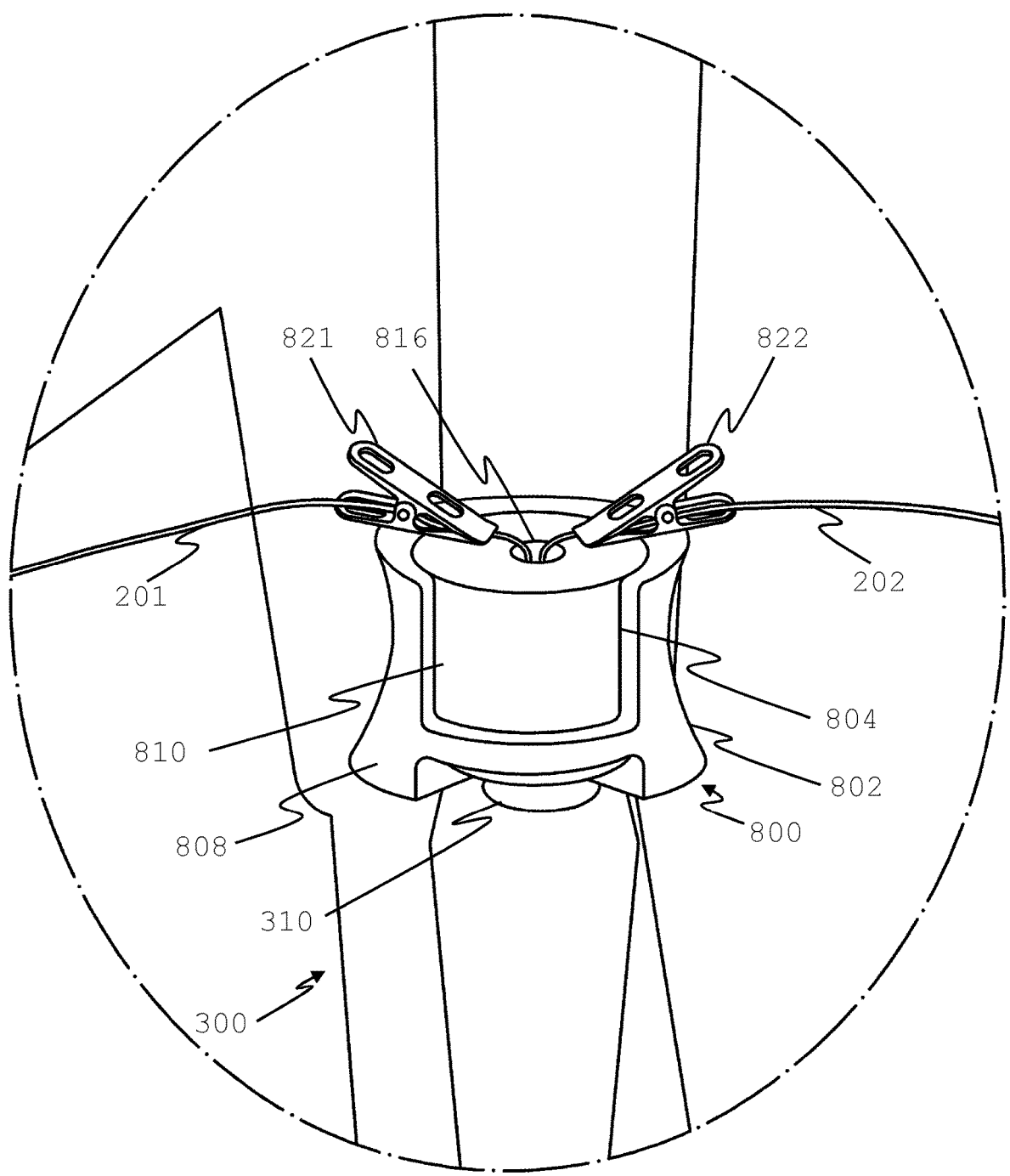
Figure 9C:
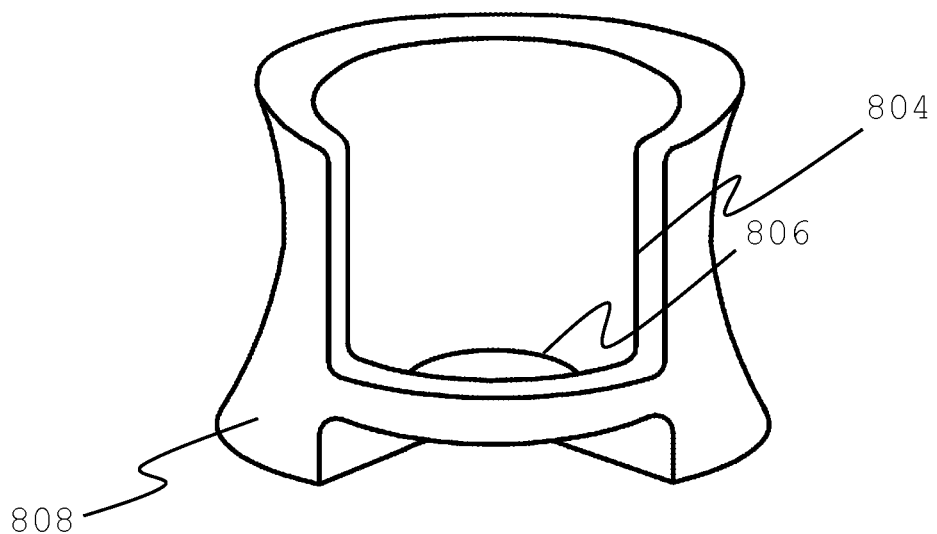

To further control the first and second sutures 201, 202 that are attached to the first and second tissue approximation clips 101, 102 respectively, the tissue approximation clip system 100 may further include a suture locking apparatus 800 as shown in FIGS. 9A-C. As shown in FIGS. 9B-C, the suture locking apparatus 800 includes an outer shell 802 which includes a cavity 804, a through-hole 806, and an attachment portion 808. The suture locking apparatus 800 may further include a suture guide 810 constructed to fit into the cavity 804 of the outer shell 802 and first and second clamps 821, 822 to hold the first and second sutures 201, 202 respectively. For further adjustment of the sutures 201, 202, either the first and second clamps 821, 822 (or both) may be operated to release the hold that the clamps 821, 822 have on the sutures 201, 202. The attachment portion 808 of the outer shell 802 is constructed to detachably attach the suture locking apparatus 800 onto the instrument channel 310 of the endoscope 300. Procedurally, the suture locking apparatus 800 is detachably coupled to a port 330 of the instrument channel 310 of the endoscope 300 prior to transport of the first tissue approximation clip 101 as shown in FIG. 9A.

As shown in FIG. 9B, the suture guide 810 includes a through-hole 816 wherein the first and second sutures 201 pass through the through-hole 806 of the outer shell 802 and the through-hole 816 of the suture guide 810. The suture guide 810 may be molded from any elastomer known in the art including, but not limited to, synthetic rubber, thermoplastic elastomers, and the like. Preferably, the suture guide 810 is molded from synthetic rubber. Additionally, the method for approximating closure of a defect may further employ the use of the suture locking apparatus 800 of FIGS. 9A-B to hold the first and second sutures 201, 202.

FIGS. 4A-L illustrate a method for approximating a tissue defect 20 using a gastrointestinal tissue approximation clip ("GI TAC") system, the method including the steps of positioning a distal end of an insertion tube 320 of an endoscope 300 towards a tissue defect inside of a patient as shown in FIG. 4A; directing, via an applicator 400, a first tissue approximation clip 101, detachably attached to the applicator 400, through an instrument channel 310 of the endoscope 300 and towards the tissue defect 20 as shown in FIG. 4B; placing the first tissue approximation clip 101 on a first location of the tissue defect 20 and clamping the first tissue approximation clip 101 thereon as shown in FIG. 4C; detaching the applicator 400 from the first tissue approximation clip 101 and withdrawing the applicator 400 from the instrument channel 310 of the endoscope 300 as shown in FIG. 4C; directing, via the applicator 400, a second tissue approximation clip 102, detachably attached to the applicator 400, through the instrument channel 310 of the endoscope 300 and towards the tissue defect 20.

With regards to the second tissue approximation clip 102, the method further includes: placing the second tissue approximation clip 102 on a second location of the tissue defect 20 and clamping the second tissue approximation clip 102 thereon; and detaching the applicator 400 from the second tissue approximation clip and withdrawing the applicator 400 from the instrument channel 310 of the endoscope 300, the results of which are shown in FIG. 4D. For this method, first and second sutures 201, 202 are attached to the first and second tissue approximation clips 101, 102 respectively as shown in FIGS. 3A-B and FIG. 4D.

Each of the first and second tissue approximation clips 101, 102 includes: a body portion 110; and a grasping portion 120 coupled to the body portion 110. The body portion 110 is detachably coupled to the applicator 400. The grasping portion 120 is configured to grasp onto tissue during the placing steps. The grasping portion 120 includes a moveable jaw that is constructed to move from a spaced-apart position to an approximated position, or move from the approximated position to the spaced-apart position. In the approximated position, the first and second jaw portions 1201, 1202 may be fully closed against each other or closed upon a portion of a tissue of a patient. Other designs and configurations with respect to the jaw portions 1201, 1202 of the grasping portion 120 may be considered that do not depart from the spirit and scope of the invention so long as the jaw is constructed to open and close whereupon closure of the jaw onto tissue provides sufficient clamping and hold onto the tissue.

Figure 4F:
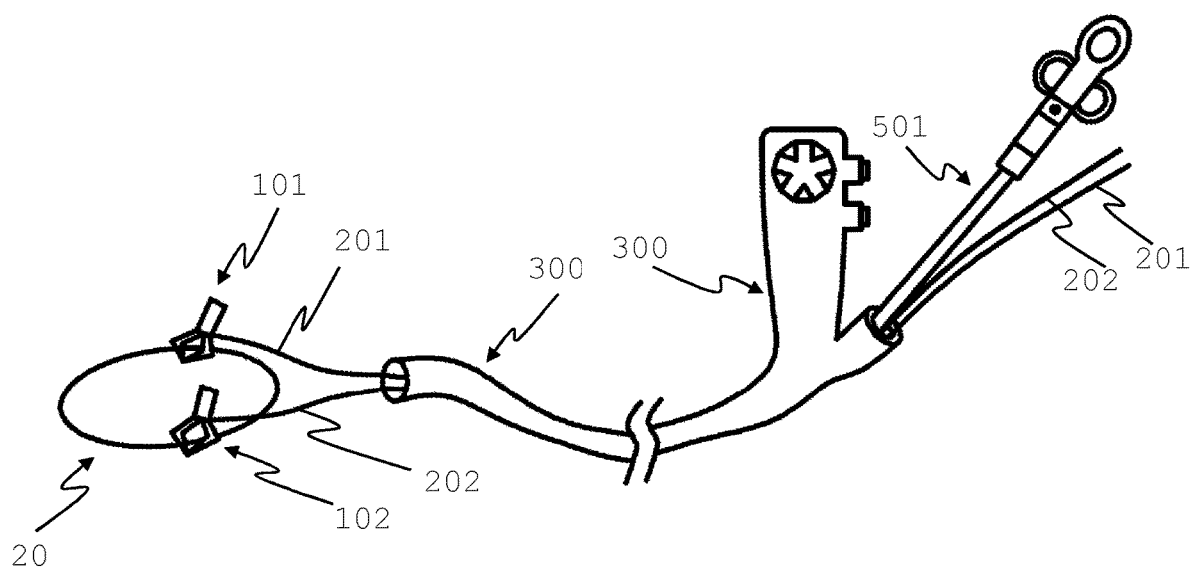
Figure 4G:
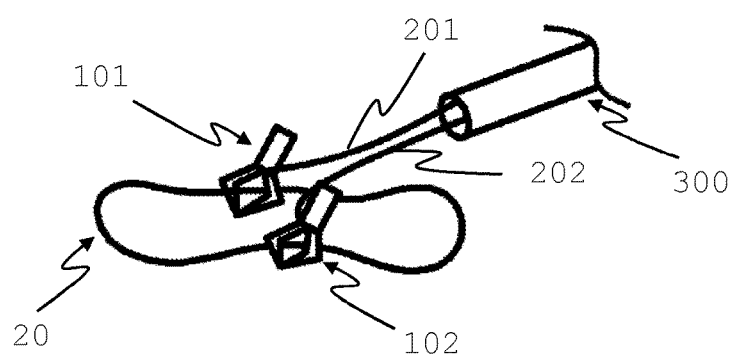
Figure 4H:
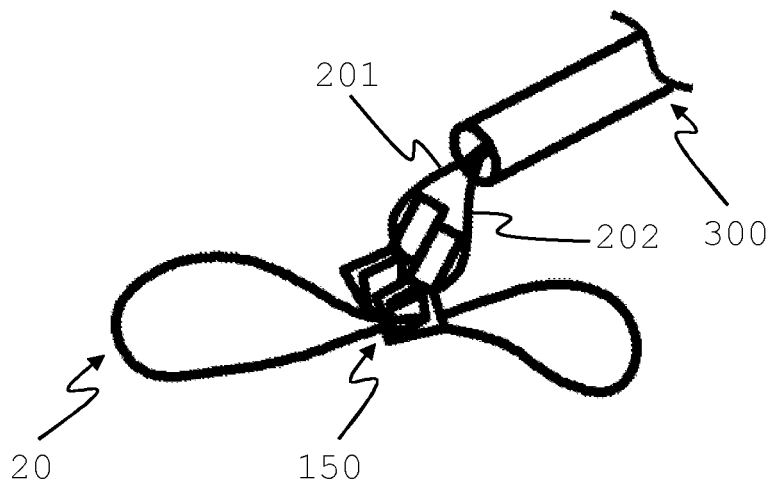
Figure 4I:
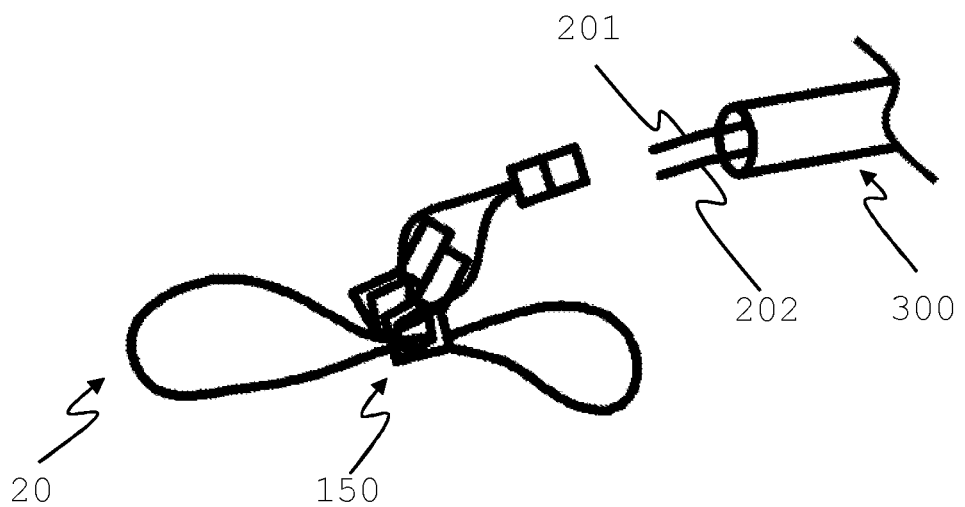
Figure 4J:
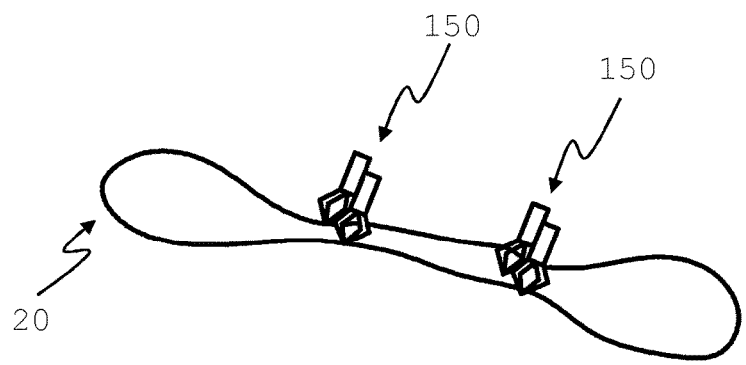
Figure 4K:
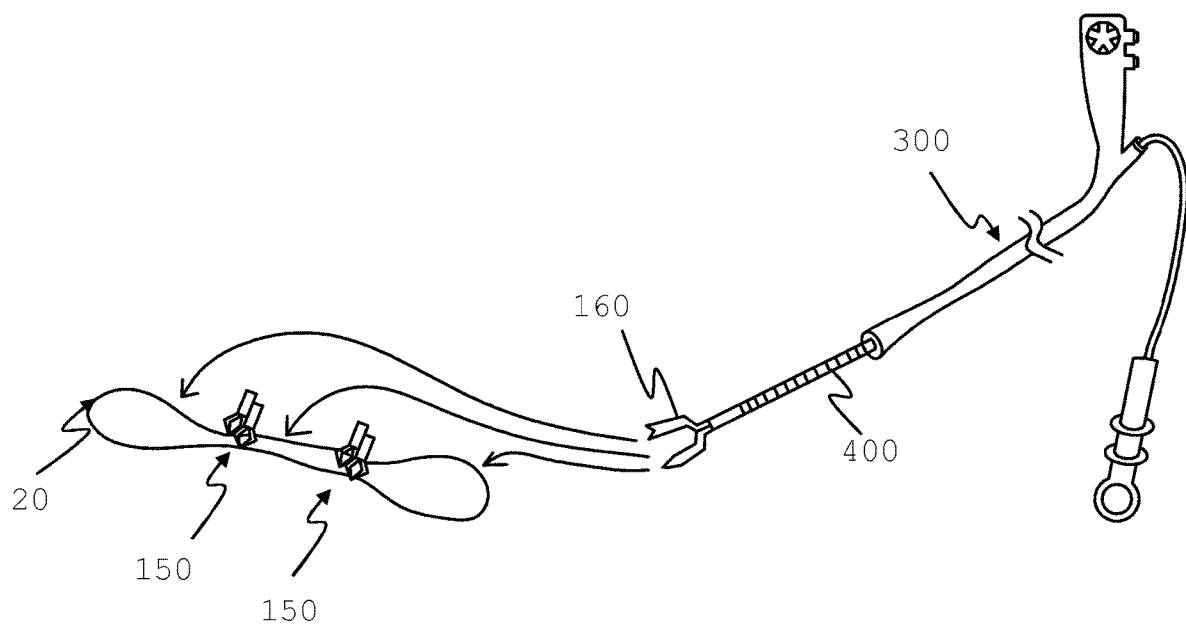

Additional steps to the method include threading the first and second sutures 201, 202, as shown in FIG. 4E, through a clip approximation means for approximating the first and second tissue approximation clips 101, 102. Further, directing the clip approximating means towards the first and second tissue approximation clips 101, 102 such that the first tissue approximation clip 101 moves towards the second tissue approximation clip 102, the second tissue approximation clip 102 moves towards the first tissue approximation clip 101, or the first and second approximation clips 101, 102 move towards each other such that the first and second tissue approximation clips 101, 102 approximates (with approximation via magnetic attraction as an option) with each other to form a tissue approximation clip complex 150 as shown in FIGS. 4F-H; and cutting, using the clip approximation means or the cutting means, the first and second sutures 201, 202 from the first and second tissue approximation clips 101, 102, wherein the first and second locations of the tissue defect 20 are approximated to each other following the directing step as shown in FIG. 4I. As shown, the clip approximation means is sized to travel through the instrument channel 310 of the endoscope 300.

In this method, the clip approximation means is a catheter device 501, a catheter device 502, or a suture adjoining clamp 601. Each of the catheter devices 501, 502 include a slidable blade 520 and a through-hole 510 which permits threading of the first and second sutures 201, 202 therethrough as shown in FIG. 5 for the catheter device 501 and as shown in FIG. 6A-E for the catheter device 502. When the catheter device 501, or the catheter device 502, is used in the cutting step, the slidable blade 520 cuts the first and second sutures 201, 202 as shown in FIGS. 5 and 6D. The suture adjoining clamp 601, as shown in FIGS. 7A-D, includes moveable arms 611, 612 where each of the arms 611, 612 of the suture adjoining clamp 601 includes a grip 614 and a through-hole 616 through which permits threading of the first and second sutures 201, 202. As shown in FIG. 4D, suture adjoining clamp 601 is detachably coupled to the applicator 410. Furthermore, the arms 611, 612 of the suture adjoining clamp 601 are movable from a spaced-apart position to an approximated position, and movable from the approximated position to the spaced-apart position. When the suture adjoining clamp 601 is used in the cutting step, the suture adjoining clamp 601 may include a cutting means in the form of a slidable sheath 620 having a sharpened edge 622 as described above. Alternatively, the cutting means is a cutting device 720 as shown in FIG. 8, which includes a tube 722 having an end 724, a side through-hole 726, and a cutting blade 728, follows the suture adjoining clamp 601 after the suture adjoining clamp 601 approximated the first and second tissue approximation clips 101, 102 into a tissue approximation complex 150 and adjoined to the tissue approximation complex 150. As shown in FIG. 8, the cutting device 720, having the first and second sutures 201, 202 threaded through the end 724 and the side through-hole 726, is brought towards the suture adjoining clamp 601 and the tissue approximation complex 150 to cut the first and second sutures 201, 202, as described above. Furthermore, the cutting device 720 may be adapted for use with the catheters 501, 502 as shown in FIGS. 5 and 6A and as described above.

With regards to the clip approximation means as the catheter device 502, as shown in FIG. 6, further includes the tube 505 which includes an end 512 and a through-hole 510; an inner rod 530 that extends from the tube 505; a ball 540 detachably coupled to the inner rod 530; and a slidable blade 520. The through-hole 510 permits threading of the first and second sutures 201, 202 therethrough. The end 512 of the tube 505 is open to permit the first and second sutures 201, 202 to pass through the opened end 512 of the tube 505. The method using this catheter device 501 may include an additional step of retracting, following the directing step and prior to the cutting step, the inner rod 530 of the catheter device 502 into the tube 505 of the catheter device 502 such that the ball 540 of the catheter device 502 snaps onto the first and second sutures 201, 202 to form a ball-and-socket complex 550 that is released following the cutting step.

Figure 4L:
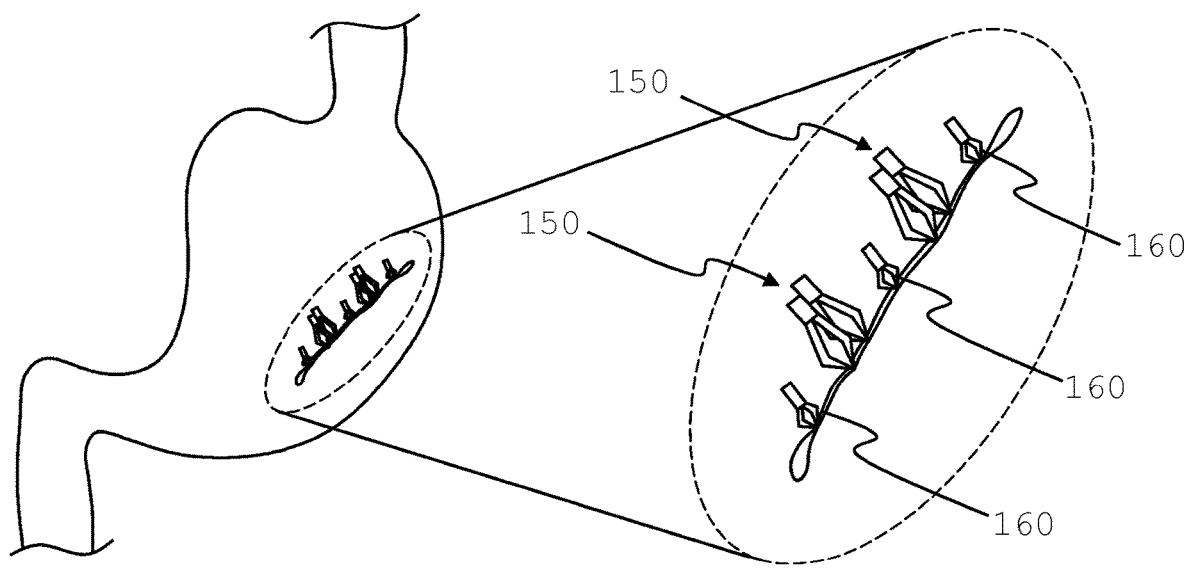

As shown in FIGS. 2B, 3A-B, 4A-L, 5, 6A-E, and 7A-D, the first and second tissue approximation clips 101, 102 adhere to each other via magnetic force or other means (the ball-and-socket complex 550 shown in FIGS. 6A-E or the suture adjoining clamp 601 shown in FIGS. 7A-D) to form a tissue approximation clip complex 150 that further approximates the tissue defect 20; the tissue approximation complex 150 may be included in a ball-and-socket complex 550 as shown in FIG. 6E or be adjoined to a suture adjoining clamp 601 as shown in FIG. 6D. As shown in FIG. 4L, at least one tissue approximation clip complex 150 is clamped along the length of the defect. Following proper clamping of the tissue approximation clip complexes 150 along the length of the defect, the defect is finally closed by applying tissue closure clips 160 at around the tissue approximation clip complex 150 of the semi-closed defect after opposing sides of the defect are brought substantially close together by at least one of the tissue approximation clip complexes 150 as shown. Alternatively, if the at least one tissue approximation clip complex 150 sufficiently approximates the defect such that the defect resembles a substantially straight or a curved line save for opposite ends of the line having a substantially small opening, then tissue closure clips 160 may be applied onto the substantially small opening of the opposite ends of the line to close them.

For all of the embodiments that include the tissue closure clips 160, the tissue closure clips 160 are preferably made from materials which do not have affinity to magnets or have minimal interaction with magnets (e.g. non-ferromagnetic metals like titanium) so as not to interfere with any adjacent tissue approximation clip complex 150 and interfere with clamping process of the tissue approximation clip 101. As with other clips and suturing systems, new epithelium grown underneath the tissue approximation clips 101, 102 will eventually push the tissue approximation clips 101, 102 off such that the tissue approximation clips 101, 102 slough off within a few weeks and then excreted through feces.

For all of the embodiments described above, any metals used in the construction of either the tissue approximation clips 101 or the tissue closure clips 160 should be made magnetic resonance imaging (MRI) safe (or at least MR conditional) as other clips in the market. Implantation of magnets in the body is generally thought not to be MRI safe. However, there are magnetic rings that may be placed laparoscopically at the esophagus/stomach junction that is considered to be "MR Conditional" for MRI systems up to 1.5 T. Approximately 89% of MRI machines in the U.S. are 1.5 T or lower, so the magnetic materials used to construct the magnetic rings may also be used for magnetic parts of the tissue approximation 101 and tissue closure clips 160 (moreover for the former) to ensure that they are MR Conditional for a large majority of MRI systems in the U.S. Moreover, most clips 101, 102, 160 should slough off within a few weeks. Additionally, simple X-rays may be ordered to see if the clips 101, 102, 160 are still adhered to the GI wall. If the clips 101, 102, 160 are still attached and alternative diagnostic procedures cannot be used, then the tissue approximation clips 101, 102 and/or tissue closure clips 160 can be removed via endoscopy or colonoscopy.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A gastrointestinal tissue approximation clip ("GI TAC") system for approximating tissue defects, the GI TAC system comprising:
    an applicator that is sized to travel through an instrument channel of an endoscope;
    first and second tissue approximation clips that are transported to first and second locations of a tissue defect respectively by the applicator to approximate the tissue defect;
    first and second sutures attached to the first and second tissue approximation clips respectively; and
    a clip approximation means for approximating the first and second tissue approximation clips,
    wherein the clip approximation means is sized to travel through the instrument channel,
    wherein the first and second tissue approximation clips are sized to travel through the instrument channel, and
    wherein the first and second tissue approximation clips are adapted to be detachably coupled to the applicator; and
    wherein each of the first and second tissue approximation clips comprises:
    a body portion; and
    a grasping portion that is coupled to the body portion,
    wherein the grasping portion includes first and second jaw portions that are constructed to move from a spaced-apart position to an approximated position, or move from the approximated position to the spaced-apart position,
    wherein the grasping portion is constructed to grasp the tissue defect, and
    wherein the body portion is constructed to be detachably coupled to the applicator;
    wherein,
    the GI TAC system further comprises a suture locking apparatus to further control the first and second sutures, wherein the suture locking apparatus comprises:
    an outer shell which includes a cavity, a through-hole, and an attachment portion;
    a suture guide that is disposed in the cavity of the outer shell; and
    first and second clamps that adjustably hold the first and second sutures respectively,
    wherein the attachment portion of the outer shell sits atop the instrument channel and is detachable from the instrument channel,
    wherein the suture guide includes a through-hole, and
    wherein the respective through-holes of the outer shell and the suture guide allows the first and second sutures pass through into the instrument channel.

2. The GI TAC system of claim 1, wherein the first and second jaw portions of the grasping portion are a rat-toothed configuration.

3. The GI TAC system of claim 1, wherein the body portions of the first and second tissue approximation clips are substantially cubic, substantially prismatic, substantially rectangular prism, substantially spherical, substantially oblate spheroidal, substantially prolate spheroidal, substantially columnar, or substantially cylindrical.

4. The GI TAC system of claim 3, wherein the body portion includes a joining means for fitting the first and second tissue approximation clips together, and
    wherein the joining means of the first tissue approximation clip is complimentary to the joining means of the second tissue approximation clip.

5. The GI TAC system of claim 1, wherein the first and second tissue approximation clips are constructed to magnetically attract each other,
wherein the clip approximation means is a catheter device which comprises a slidable blade and a through-hole,
wherein the through-hole of the catheter device permits the first and second sutures to pass therethrough,
wherein the slidable blade is to cut the first and second sutures,
wherein the catheter device brings the first and second sutures closer together such that the first tissue approximation clip substantially and magnetically couples to the second tissue approximation clip.

6. The GI TAC system of claim 1, the clip approximation means is a catheter device which comprises:
a tube which includes an end and a through-hole;
an inner rod that extends from the tube;
a ball detachably coupled to the inner rod; and
a slidable blade to cut the first and second sutures,
wherein the end of the tube is open to permit the first and second sutures to pass through the opened end of the tube,
wherein, when the inner rod is retracted into the tube, the ball is constructed to snap onto the first and second sutures and detach from the inner rod to form a ball-and-socket complex which approximates the first and second tissue approximation clips.

7. The GI TAC system of claim 1, wherein the clip approximating means is a suture adjoining clamp,
wherein the suture adjoining clamp includes movable arms wherein each of the arms includes a grip and a through-hole through which threading of the first and second sutures is permitted,
wherein the arms of the suture adjoining clamp are movable from a spaced-apart position to an approximated position, and movable from the approximated position to the spaced-apart position,
wherein, when the first and second sutures are between the grips and the arms are in the approximated position, the grips meet each other and hold the first and second sutures.

8. The GI TAC system of claim 7, further comprising a suture adjoining clamp applicator that transports the suture adjoining clamp through the instrument channel,
wherein the suture adjoining clamp applicator includes a slidable sheath having a sharpened outer edge,
wherein a width of the slidable sheath is greater than a width of the suture adjoining clamp, and
wherein, the outer edge of the slidable sheath is configured to slide across the first and second sutures that are presented by at least one of the through-holes of the arms to cut the first and second sutures.

9. The GI TAC system of claim 7, further comprising a cutting device which includes:
a tube having an end;
a through-hole; and
a blade to cut the first and second sutures,
wherein the cutting device is sized to pass through the instrument channel of the endoscope,
wherein the blade is constructed to slide up to open the end of the tube, and
wherein the end, when opened, and the through-hole permits the first and second sutures to pass therethrough.

10. A gastrointestinal tissue approximation clip ("GI TAC") system for approximating tissue defects, the GI TAC system comprising:
an applicator that is sized to travel through an instrument channel of an endoscope;
first and second tissue approximation clips that are transported to first and second locations of a tissue defect respectively by the applicator to approximate the tissue defect; and
first and second sutures attached to the first and second tissue approximation clips respectively,
wherein the first and second tissue approximation clips are sized to travel through the instrument channel, and
wherein the first and second tissue approximation clips are adapted to be detachably coupled to the applicator; and
wherein each of the first and second tissue approximation clips comprises:
a body portion; and
a grasping portion that is coupled to the body portion,
wherein the grasping portion includes a moveable jaw that is constructed to move from a spaced-apart position to an approximated position, or move from the approximated position to the spaced-apart position, and
wherein the body portion is constructed to be detachably coupled to the applicator;
wherein,
the GI TAC system further comprises a suture locking apparatus to further control the first and second sutures, wherein the suture locking apparatus comprises:
an outer shell which includes a cavity, a through-hole, and an attachment portion;
a suture guide that is disposed in the cavity of the outer shell; and
first and second clamps that adjustably hold the first and second sutures respectively,
wherein the attachment portion of the outer shell sits atop the instrument channel and is detachable from the instrument channel,
wherein the suture guide includes a through-hole, and
wherein the respective through-holes of the outer shell and the suture guide allows the first and second sutures pass through into the instrument channel.

11. The GI TAC system of claim 10, further comprising a catheter device which includes a slidable blade and a through-hole,
wherein the first and second tissue approximation clips are constructed to magnetically attract each other,
wherein the catheter device is sized to travel through the instrument channel,
wherein the through-hole of the catheter device permits the first and second sutures to pass therethrough,
wherein the slidable blade is to cut the first and second sutures from the first and second tissue approximation clips respectively,
wherein the catheter device brings the first and second sutures closer together such that the first tissue approximation clip substantially and magnetically couples to the second tissue approximation clip.

12. The GI TAC system of claim 10, further comprising a catheter device which comprises:
a tube which includes an end and a through-hole;
an inner rod that extends from the tube;
a ball detachably coupled to the inner rod; and
a slidable blade to cut the first and second sutures,
wherein the catheter device is sized to travel through the instrument channel,
wherein the end of the tube is open to permit the first and second sutures to pass through the opened end of the tube, wherein, when the inner rod is retracted into the tube, the ball is constructed to snap onto the first and second sutures and detach from the inner rod to form a ball-and-socket complex which approximates the first and second tissue approximation clips.

13. The GI TAC system of claim 10, further comprising:
a suture adjoining clamp applicator which includes a cutting means for cutting the first and second sutures; and
a suture adjoining clamp which includes moveable arms wherein each of the arms includes a grip and a through-hole through which threading of the first and second sutures is permitted,
wherein the suture adjoining clamp applicator transports the suture adjoining clamp through the instrument channel,
wherein the cutting means is sized to pass through the instrument channel, and
wherein, when the first and second sutures are between the grips and the arms are moved and approximated together, the grips meet each other and hold the first and second sutures.

14. A method for approximating a tissue defect using a gastrointestinal tissue approximation clip ("GI TAC") system according to claim 10, the method comprising the steps of:
positioning a distal end of an insertion tube of an endoscope towards a tissue defect inside of a patient;
directing, via an applicator, a first tissue approximation clip, detachably attached to the applicator, through an instrument channel of the endoscope and towards the tissue defect;
placing the first tissue approximation clip on a first location of the tissue defect and clamping the first tissue approximation clip thereon;
detaching the applicator from the first tissue approximation clip and withdrawing the applicator from the instrument channel of the endoscope;
directing, via the applicator, a second tissue approximation clip, detachably attached to the applicator, through the instrument channel of the endoscope and towards the tissue defect;
placing the second tissue approximation clip on a second location of the tissue defect and clamping the second tissue approximation clip thereon; and
detaching the applicator from the second tissue approximation clip and withdrawing the applicator from the instrument channel of the endoscope,
wherein first and second sutures are attached to the first and second tissue approximation clips respectively, and
wherein each of the first and second tissue approximation clips includes:
a body portion; and
a grasping portion coupled to the body portion,
wherein the body portion is detachably coupled to the applicator,
wherein the grasping portion includes a moveable jaw that is constructed to move from a spaced-apart position to an approximated position, or move from the approximated position to the spaced-apart position, and
wherein the grasping portion is configured to grasp onto tissue during the placing steps.

15. The method of claim 14, further comprising the steps of:
threading the first and second sutures through a clip approximation means for approximating the first and second tissue approximation clips;
directing the clip approximating means towards the first and second tissue approximation clips such that the first tissue approximation clip moves towards the second tissue approximation clip, the second tissue approximation clip moves towards the first tissue approximation clip, or the first and second approximation clips move towards each other such that the first and second tissue approximation clips magnetically approximates with each other to form a tissue approximation clip complex; and
cutting, using the clip approximation means or a cutting means, the first and second sutures from the first and second tissue approximation clips,
wherein the first and second tissue approximation clips are constructed to magnetically attract each other,
wherein the first and second locations of the tissue defect are approximated to each other following the directing step, and
wherein the clip approximation means and the cutting means are sized to travel through the instrument channel of the endoscope.

16. The method of claim 14, further comprising the steps of:
threading the first and second sutures through a clip approximation means for approximating the first and second tissue approximation clips;
directing the clip approximating means towards the first and second tissue approximation clips such that the clip approximation means causes the first tissue approximation clip to move towards the second tissue approximation clip, the second tissue approximation clip to move towards the first tissue approximation clip, or the first and second approximation clips to move towards each other such that the first and second approximation clips approximates with each other; and
cutting, using the clip approximation means or a cutting means, the first and second sutures from the first and second tissue approximation clips,
wherein the first and second locations of the tissue defect are approximated to each other following the directing step, and
wherein the clip approximation means and the cutting means are sized to travel through the instrument channel of the endoscope,
wherein the clip approximation means is a catheter device or a suture adjoining clamp,
wherein the catheter device includes a slidable blade and a through-hole which permits threading of the first and second sutures therethrough,
wherein the suture adjoining clamp includes moveable arms wherein each of the arms of the suture adjoining clamp includes a grip and a through-hole through which permits threading of the first and second sutures,
wherein the arms of the suture adjoining clamp are movable from a spaced-apart position to an approximated position, and movable from the approximated position to the spaced-apart position,
wherein the suture adjoining clamp is detachably coupled to the applicator,
wherein, when the catheter device is used in the cutting step, the slidable blade of the catheter device cuts the first and second sutures, and wherein, when the suture adjoining clamp is used in the cutting step, the cutting means for cutting the first and second sutures is deployed.

17. The method of claim 16, further comprising the step of:
retracting, following the directing step and prior to the cutting step, an inner rod of the catheter device into the tube of the catheter device such that a ball of the catheter device snaps onto the first and second sutures to form a ball-and-socket complex,
wherein the catheter device further includes:
the tube which includes an end and the through-hole;
the inner rod that extends from the tube; and
the ball detachably coupled to the inner rod,
wherein the end of the tube is open to permit the first and second sutures to pass through the open end of the tube.

\* \* \* \* \*